(12) United States Patent
Huffmaster et al.

(10) Patent No.: US 11,957,397 B2
(45) Date of Patent: Apr. 16, 2024

(54) CRYOGENIC DEVICE WITH QUICK-CONNECT NEEDLE PROBES

(71) Applicant: Pacira CryoTech, Inc., Parsippany, NJ (US)

(72) Inventors: Andrew Huffmaster, Fremont, CA (US); Erika Danielle Anderson-Bolden, Fremont, CA (US); Eric J. Darby, San Francisco, CA (US); Eric Theodore Johansson, Dublin, CA (US); Paul Tanaka-Roche, San Jose, CA (US); Jeff Gamelsky, Palo Alto, CA (US)

(73) Assignee: Pacira CryoTech, Inc., Tampa, FL (US)

( * ) Notice: Subject to any disclaimer, the term of this patent is extended or adjusted under 35 U.S.C. 154(b) by 558 days.

(21) Appl. No.: 17/081,437

(22) Filed: Oct. 27, 2020

(65) Prior Publication Data
US 2021/0121219 A1 Apr. 29, 2021

Related U.S. Application Data

(60) Provisional application No. 62/927,375, filed on Oct. 29, 2019.

(51) Int. Cl.
*A61B 18/02* (2006.01)
*A61B 17/00* (2006.01)
(Continued)

(52) U.S. Cl.
CPC .... *A61B 18/02* (2013.01); *A61B 2017/00424* (2013.01); *A61B 2017/00526* (2013.01);
(Continued)

(58) Field of Classification Search
CPC .......... A61B 18/02; A61B 2018/00023; A61B 2018/00172; A61B 2018/0293;
(Continued)

(56) References Cited

U.S. PATENT DOCUMENTS

| 4,236,518 A | 12/1980 | Floyd |
| 7,160,291 B2 | 1/2007 | Damasco et al. |

(Continued)

FOREIGN PATENT DOCUMENTS

| CN | 103349813 B | 4/2015 |
| EP | 2826498 A1 | 1/2015 |

(Continued)

*Primary Examiner* — Khadijeh A Vahdat
(74) *Attorney, Agent, or Firm* — Kilpatrick Townsend & Stockton LLP

(57) ABSTRACT

A cryogenic device with a cartridge holder for a cryogen cartridge, cryogen cartridge is coupleable to a cryogen pathway; a probe receptacle for receiving a needle probe, wherein the probe receptacle is configured to couple the needle probe to the cryogen cartridge via the cryogen pathway, and wherein the needle probe comprises: one or more needles having needle lumens disposed therein; a probe extension extending proximally, the probe extension having a probe lumen disposed therein, the probe lumen including an elongate element that extends from a proximal end to a distal end, wherein the probe lumen is coupled to the needle lumens at the distal end, and the cryogen pathway at a first location in between the proximal end and the distal end. Various connection mechanisms for securing needle probes to a handpiece portion are disclosed.

15 Claims, 18 Drawing Sheets

(51) Int. Cl.
*A61B 17/34* (2006.01)
*A61B 18/00* (2006.01)

(52) U.S. Cl.
CPC ............... *A61B 2017/3413* (2013.01); *A61B 2018/00023* (2013.01); *A61B 2018/0293* (2013.01)

(58) Field of Classification Search
CPC .......... A61B 2017/00424; A61B 2017/00526; A61B 2017/3413; A61B 2090/3925
See application file for complete search history.

(56) References Cited

U.S. PATENT DOCUMENTS

| | | | |
|---|---|---|---|
| 7,713,266 B2 | 5/2010 | Elkins et al. | |
| 7,819,860 B2* | 10/2010 | Wittenberger | A61B 17/29 606/23 |
| 7,850,683 B2 | 12/2010 | Elkins et al. | |
| 7,998,137 B2 | 8/2011 | Elkins et al. | |
| 8,298,216 B2 | 10/2012 | Burger et al. | |
| 8,409,185 B2 | 4/2013 | Burger et al. | |
| 8,461,108 B2 | 6/2013 | Hsu et al. | |
| 9,017,318 B2 | 4/2015 | Fourkas et al. | |
| 9,039,688 B2 | 5/2015 | Palmer, III et al. | |
| 9,066,712 B2 | 6/2015 | Reynolds et al. | |
| 9,072,498 B2 | 7/2015 | Elkins et al. | |
| 9,155,584 B2 | 10/2015 | Fourkas et al. | |
| 9,241,753 B2 | 1/2016 | Fourkas et al. | |
| 9,254,162 B2 | 2/2016 | Burger et al. | |
| 9,295,512 B2 | 3/2016 | Allison et al. | |
| 9,314,290 B2 | 4/2016 | Fourkas et al. | |
| 9,345,526 B2 | 5/2016 | Elkins et al. | |
| 9,610,112 B2 | 4/2017 | Karnik et al. | |
| 9,668,800 B2 | 6/2017 | Karnik et al. | |
| 10,016,229 B2 | 7/2018 | Carnell et al. | |
| 10,085,789 B2 | 10/2018 | Carnell et al. | |
| 10,085,881 B2 | 10/2018 | Karnik et al. | |
| 10,130,409 B2 | 11/2018 | Hinton et al. | |
| 10,314,739 B2 | 6/2019 | Allison et al. | |
| 10,470,813 B2 | 11/2019 | Allison et al. | |
| 10,596,030 B2 | 3/2020 | Karnik et al. | |
| 10,888,366 B2 | 1/2021 | Allison | |
| 2007/0084742 A1* | 4/2007 | Miller | A61B 50/20 206/438 |
| 2008/0154254 A1* | 6/2008 | Burger | A61B 18/02 606/23 |
| 2009/0054773 A1* | 2/2009 | Shizuka | A61B 18/1492 606/33 |
| 2010/0004669 A1* | 1/2010 | Smith | A61B 17/320092 606/169 |
| 2012/0089211 A1 | 4/2012 | Curtis et al. | |
| 2012/0259322 A1 | 10/2012 | Fourkas et al. | |
| 2013/0190745 A1* | 7/2013 | Fourkas | A61B 18/02 606/25 |
| 2017/0239086 A1 | 8/2017 | Karnik | |
| 2018/0116705 A1 | 5/2018 | Lee et al. | |
| 2018/0235805 A1 | 8/2018 | Burger et al. | |
| 2019/0038459 A1 | 2/2019 | Karnik et al. | |
| 2019/0142494 A1 | 5/2019 | Cross et al. | |

FOREIGN PATENT DOCUMENTS

| | | |
|---|---|---|
| WO | 2009128014 A1 | 10/2009 |
| WO | 2015069792 A1 | 5/2015 |
| WO | 2016145452 A1 | 9/2016 |

* cited by examiner

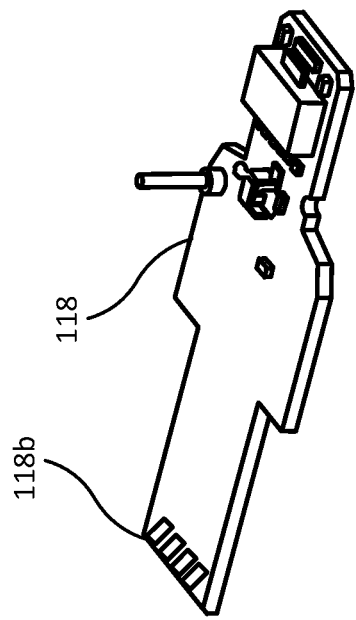
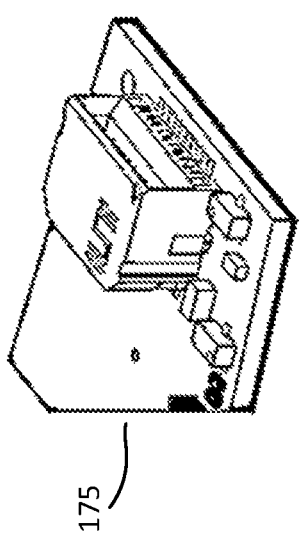
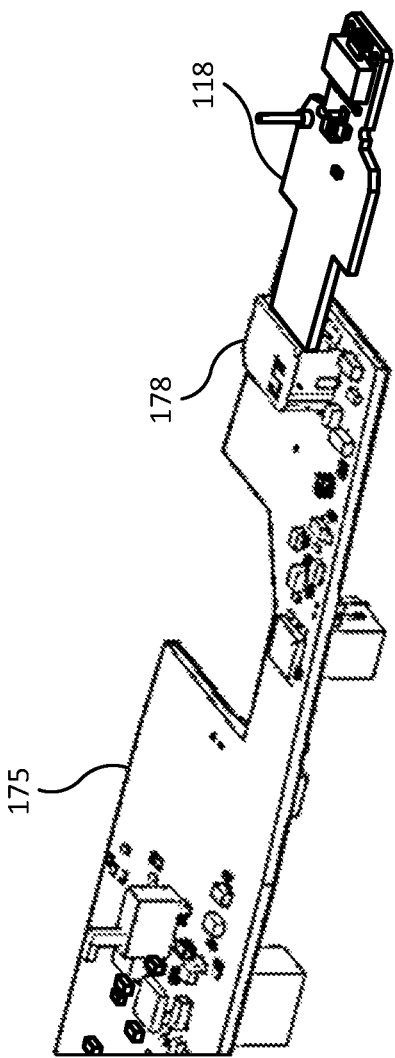
FIG. 2B
FIG. 2C

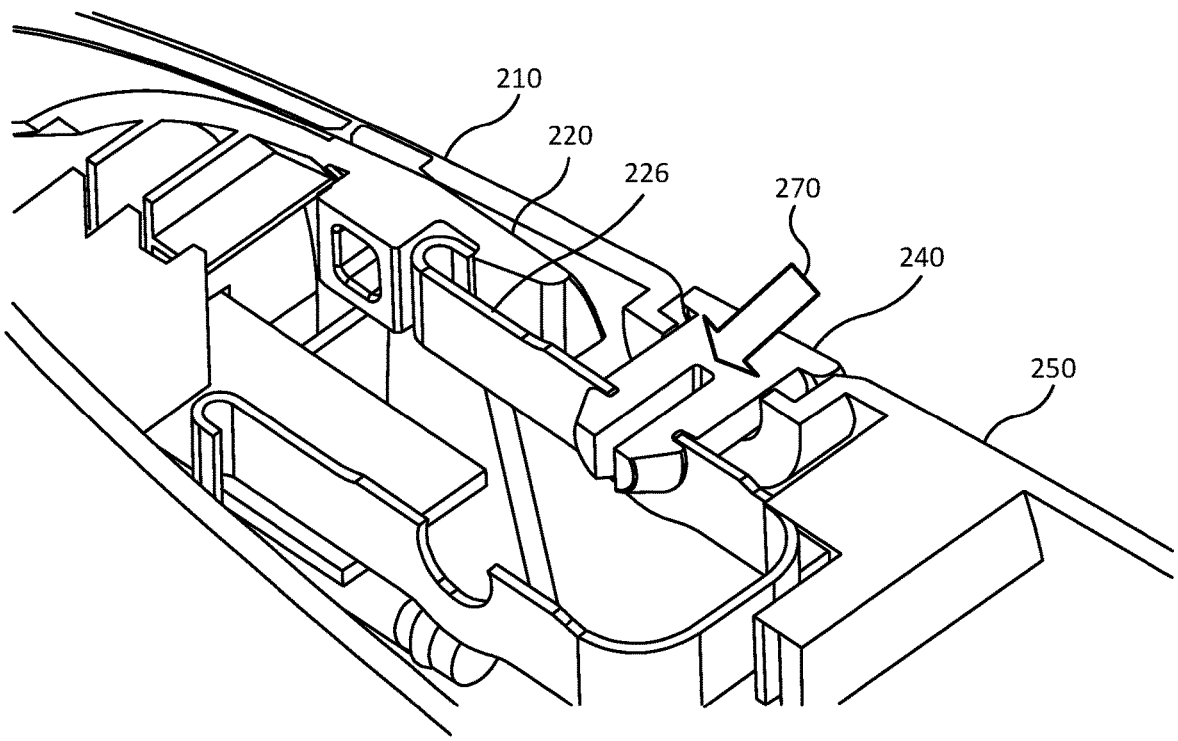
FIG. 2F
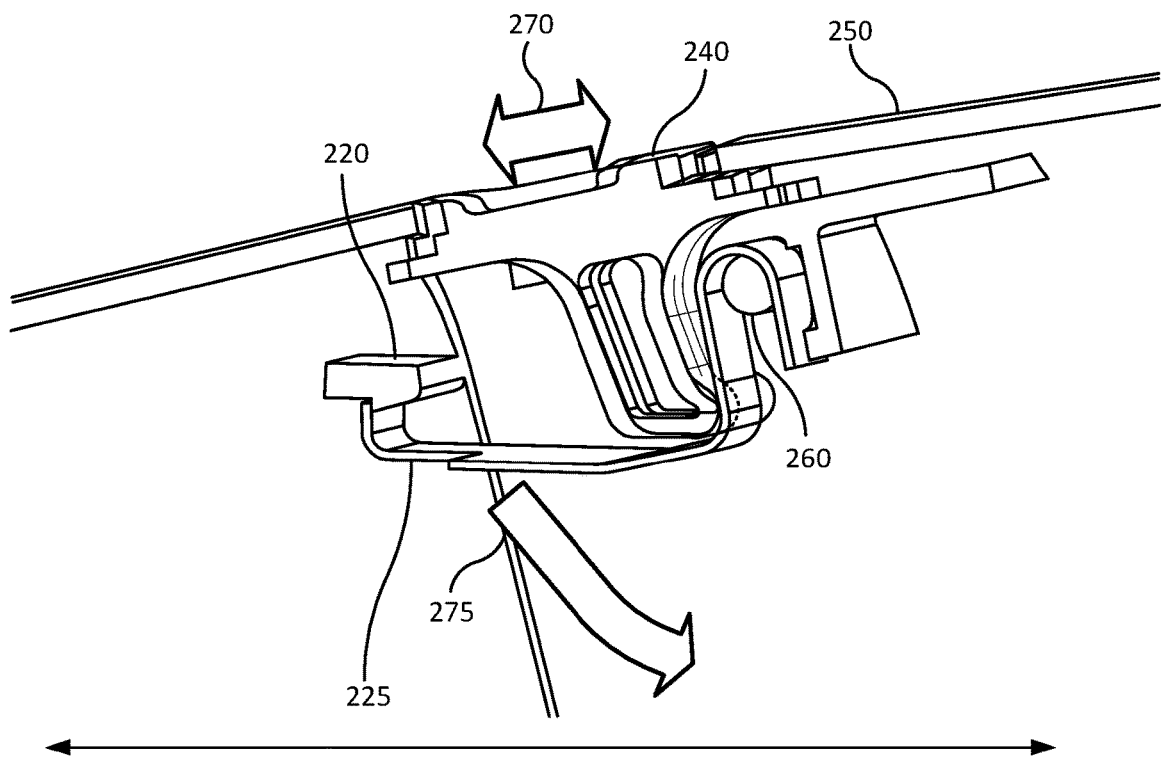
Distal  FIG. 2G  Proximal

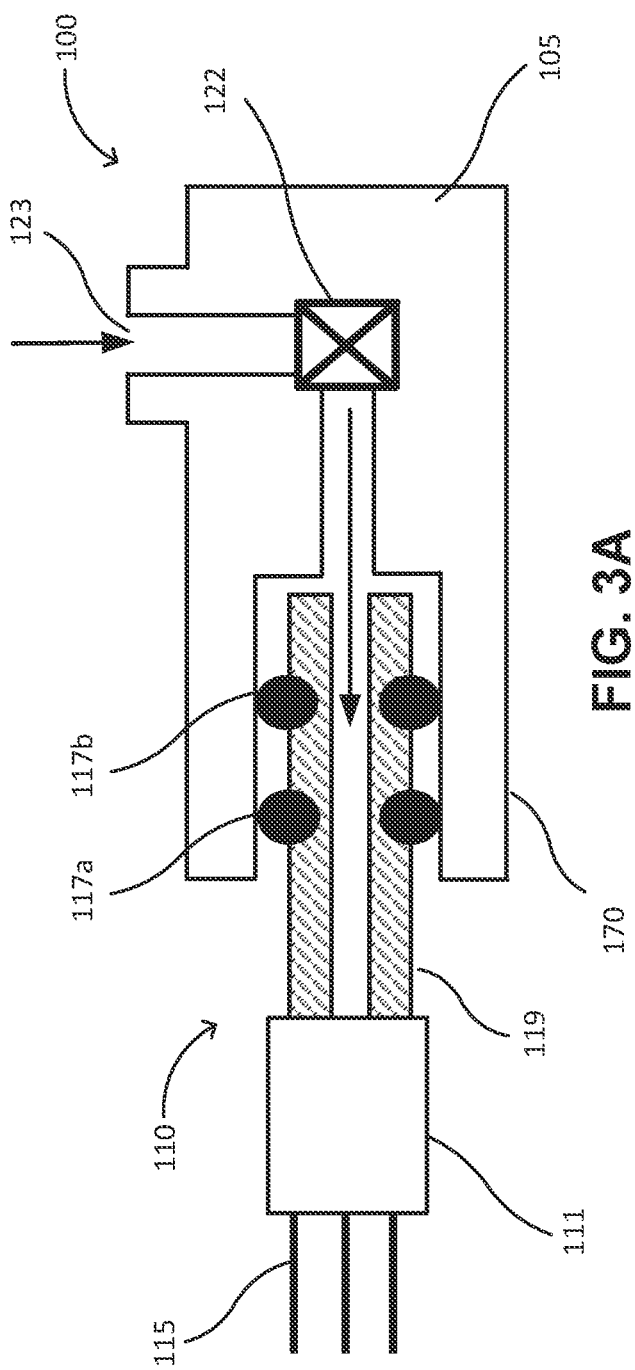
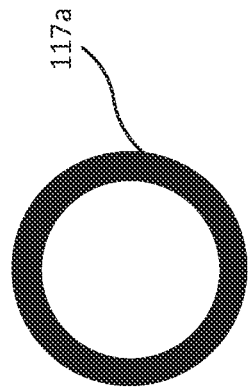
FIG. 3A
FIG. 3B

CRYOGENIC DEVICE WITH QUICK-CONNECT NEEDLE PROBES

CROSS-REFERENCES TO RELATED APPLICATIONS

The present application claims the benefit of U.S. Provisional Appln No. 62/927,375 filed Oct. 29, 2019; the disclosure of which is incorporated herein by reference in its entirety for all purposes.

RELATED FIELDS

Devices, systems, and methods for cooling tissue for therapeutic purposes, including nerves for treating pain.

BACKGROUND

The present disclosure is generally directed to medical devices, systems, and methods for cryotherapy. More specifically, the present disclosure relates to cryogenically cooling target tissues of a patient so as to degenerate, inhibit, remodel, or otherwise affect a target tissue to achieve a desired change in its behavior or composition. Cryogenic cooling of neural tissues has been shown to be effective in treating a variety of indications including pain (e.g., occipital and other neuralgias, neuromas, osteoarthritis), spasticity, and joint stiffness, among others. For example, cooling neural tissues has been found to degenerate or inhibit nerves that are instrumental in causing these conditions. Cryogenic cooling has also been employed to address cosmetic conditions, for example, by inhibiting undesirable and/or unsightly effects on the skin (such as lines, wrinkles, or cellulite dimples) or on other surrounding tissue.

In light of the above, cryogenic devices with needle probes have emerged as a mode of therapeutically cooling target tissues for treating a variety of indications. The needle probes of such devices are typically inserted into a patient's skin adjacent to a target tissue. Some cryogenic devices may include a cryogen that may be either injected into the target tissue via openings in needles of their needle probes, such that the target tissue is cooled directly by the cryogen. Other cryogenic probes may include closed needle tips, in which case the needles may be cooled (e.g., by a flow of the cryogen), and the target tissue adjacent to the cooled needles may thereby be cooled by conduction. These cryogenic probes have proved to be effective in creating cryozones within a patient at or around target tissues with precision, convenience, and reliability.

BRIEF SUMMARY

This disclosure relates to improved medical devices, systems, and methods. Many of the devices and systems described herein will be beneficial for cryotherapy using a cryogenic device. Various features of such a cryogenic device are described herein.

In some embodiments, a cryogenic device may include a cartridge holder for holding a cryogen cartridge comprising a cryogen, cryogen cartridge is coupleable to a cryogen pathway; and a probe receptacle configured to receive a needle probe, wherein the probe receptacle is configured to couple the needle probe to the cryogen cartridge via the cryogen pathway. The needle probe may include one or more needles having needle lumens disposed therein; a probe extension extending proximally, the probe extension having a probe lumen disposed therein, the probe lumen including an elongate element that extends from a proximal end to a distal end. The probe lumen may be coupled to the needle lumens at the distal end. The probe lumen may also be coupled to the cryogen pathway at a first location in between the proximal end and the distal end.

In some embodiments, the needle probe may include a first sealing element at a proximal side of the first location and a second sealing element at a distal side of the first location. The first and second sealing elements may be configured to seal the probe receptacle at the proximal and distal sides of the first location. They may also be configured to aid with retaining or securing the needle probe within the probe receptacle. The first and/or second sealing elements may be O-rings.

In some embodiments, the cryogenic device may include a passageway terminating at the proximal end of the probe lumen, wherein the passageway is exposed to ambient air. As a result, the proximal end of the probe extension may be exposed to ambient air.

In some embodiments, the cryogenic device may include a supply valve disposed along the cryogen pathway between the cryogen cartridge and the probe receptacle.

In some embodiments, the cryogenic pathway may include a bore through an internal chassis. An interior surface of the cryogenic pathway may include a metal (e.g., aluminum) configured to reduce the number of nucleation sites and the formation of bubbles from vaporization of the cryogen. For example, the internal chassis may be made of aluminum (or an aluminum alloy), such that at least a portion of the cryogenic pathway that is formed by the bore through the internal chassis is made of aluminum (or an aluminum alloy).

In some embodiments, the cartridge holder and the probe receptacle may be housed in a single handpiece capable of being held by a user. In some embodiments, a piercing point may be integrated into the handpiece, wherein the piercing point may be configured to pierce the cryogen cartridge when the cryogen cartridge is disposed within the cartridge holder.

In some embodiments, the handpiece may include an elongate housing extending along an axis. The elongate housing of the handpiece may include a movable cartridge door fixed to the elongate housing along the axis of the elongate housing, wherein the cartridge door is configured to move from an open position for allowing the cartridge holder to receive the cryogen cartridge to a closed position for securing the cryogen cartridge within the elongate housing. In some embodiments, the cartridge door may be fixed to the elongate housing such that it is configured to swivel from the open position to the closed position.

In some embodiments, the handpiece may include an elongate housing extending along an axis. The handpiece may be configured to rest substantially horizontally along the axis on a charging cradle to receive charging energy from the charging cradle.

In some embodiments, the cryogenic device may include a processor located within the handpiece. The processor may be configured to receive a probe descriptor information from the needle probe, wherein the processor is further configured to determine that the needle probe is of a first probe type of a plurality of probe types.

In some embodiments, the needles of the needle probe may include one or more depressions configured to make one or more portions of the needles echogenic so as to allow for visualization of the needles using ultrasound. In some embodiments, the needles may include depressions or projections having designs (e.g., polygonal designs) with sharp corners that may be particularly suitable in some cases for detection using ultrasound. For example, some or all of the depressions or projections may be of a polygonal design that are of a diamond shape or a star shape.

In some embodiments, the cryogenic device may be adapted for quick replacement of needle probes. Each needle probe may be disposed within a needle probe housing that may be secured to a handpiece portion of the cryogenic device. The needle probe housing may be removed and replaced with a different needle probe housing. A first needle probe housing may be secured to a handpiece portion of the cryogenic device by causing a clip element of the handpiece portion to engage a first snap element of the first needle probe housing. The clip element may include an elongate portion and a first retaining portion at an end of the elongate portion. The first snap element may include an elongate portion and a second retaining portion configured to engage the first retaining portion. The clip element may be configured to be in an engaging position or a disengaging position, wherein the engaging position is configured to cause the clip element engage the first snap element of the first needle probe housing, and wherein the disengaging position is configured to cause the clip element to disengage the first snap element. An input element coupled to the clip element may be actuated (e.g. by a user), wherein the actuation causes the clip element to move to the disengaging position. The first needle probe housing may be separated from the handpiece portion. A second needle probe housing may then be secured to the handpiece portion. In some embodiments, a second snap element of a second needle probe housing may be pushed against the clip element, causing the second snap element to temporarily deform so as to traverse a barrier effectuated by the first retaining portion of the clip element. The clip element may be caused to engage the second snap element of the second needle probe. The second needle probe housing may be secured to the handpiece portion.

In some embodiments, securing the second needle probe housing to the handpiece portion may include coupling a needle probe of the second needle probe housing to a cryogen pathway of the handpiece portion, wherein the needle probe is coupled at a first location that is between a proximal end and a distal end of a probe lumen of the needle probe. In some embodiments, the clip element may be biased toward the engaging position by a spring, and wherein actuating the input element compresses the spring. In some embodiments, the clip element may include a flat spring biased toward the engaging position, and actuating the input element deforms the flat spring, where the flat spring may include two or more prongs, each prong having a first retaining portion configured to engage a corresponding second retaining portion of the first snap element. In some embodiments, the clip element comprises a pivoting rigid plastic or metal latch that is biased toward the engaging position by a separate torsional spring. In some embodiments, actuating the input element rotates the latch to release the first snap element, wherein the second retaining portion of the first snap element comprises a hook feature configured to engage or disengage the first retaining portion of the clip element. In some embodiments, the input element may include a button disposed on an exterior of the handpiece portion. In some embodiments, the input element may include a sliding element configured to slide between a proximal location and a distal location, wherein the proximal location corresponds to one of the engaging position or the disengaging position, and the distal location corresponds to the other one of the engaging position or the disengaging position.

In some embodiments, the needle probes themselves may be removed and replaced. A probe receptacle may include a protrusion that may be used to retain a first needle probe within the probe receptacle. For example, the protrusion may be part of a latch mechanism that is configured to bolt into needle probes (e.g., the first needle probe). As another example, the protrusion may be part of a clamp mechanism that is configured to apply radially inward or outer force against (e.g., the first needle probe). In alternative embodiments, the protrusion may be on the first needle probe. The protrusion may be moved from a closed position to an open position, wherein the closed position is configured to retain a first needle probe within the probe receptacle, and wherein the open position is configured to release the first needle probe from the probe receptacle. In some embodiments, moving the protrusion to the open position may include actuating a button element or some other suitable user input element. The first needle probe may be removed from the probe receptacle. A second needle probe may then be inserted into the probe receptacle. The needle probes (e.g., the second needle probe) may include a probe lumen therein having a proximal end and a distal end. Insertion of a needle probe (e.g., the second needle probe) may cause the needle probe to be coupled to a cryogen pathway at a first location that is between the proximal end and the distal end of the probe lumen. The protrusion may be moved to a closed position (e.g., to secure the second needle probe within the probe receptacle).

BRIEF DESCRIPTION OF THE DRAWINGS

FIGS. 2B-2C illustrate an example embodiment of a port of a PCBA of a handpiece portion receiving a proximal portion of a PCBA of a needle probe.

FIGS. 2D-2I illustrate example embodiments of quick-connect mechanisms for quick connection and/or disconnection of needle probes from a handpiece portion of a cryogenic device.

FIG. 3A illustrates a cross-section schematic of a configuration for coupling a lumen of an example needle probe to a cryogen pathway of a cryogenic device.

FIG. 3B is a close-up view of an O-ring of FIG. 3A from a different perspective.

DETAILED DESCRIPTION

The present disclosure describes cryogenic devices that may be used to deliver a cryotherapy to patients. In some embodiments, the described cryogenic devices may include needles for delivering cryotherapy subcutaneously to target particular tissues for treating a variety of conditions. For example, the cryogenic devices may include needles that are configured to be inserted near peripheral nerves to deliver cryotherapy to the peripheral nerves to treat pain, spasticity, or other such conditions that may be improved by such therapy. More information about the use of cryotherapy for alleviation of pain or spasticity, may be found in U.S. Pat. No. 8,298,216 filed Nov. 14, 2008; U.S. Pat. No. 9,610,112 filed Mar. 18, 2014; U.S. Pat. No. 10,085,789 filed Mar. 13, 2017; U.S. Patent Publn No. 20190038459 filed Sep. 14, 2018, the full disclosures of which are incorporated herein by reference in their entirety for all purposes. The cryogenic devices may also be used for prophylactic treatment such as disruption or prevention of neuromas, for example, as described in U.S. Pat. No. 10,470,813 filed Mar. 14, 2016, the full disclosure of which is incorporated herein by reference in their entirety for all purposes.

Figure 1A:
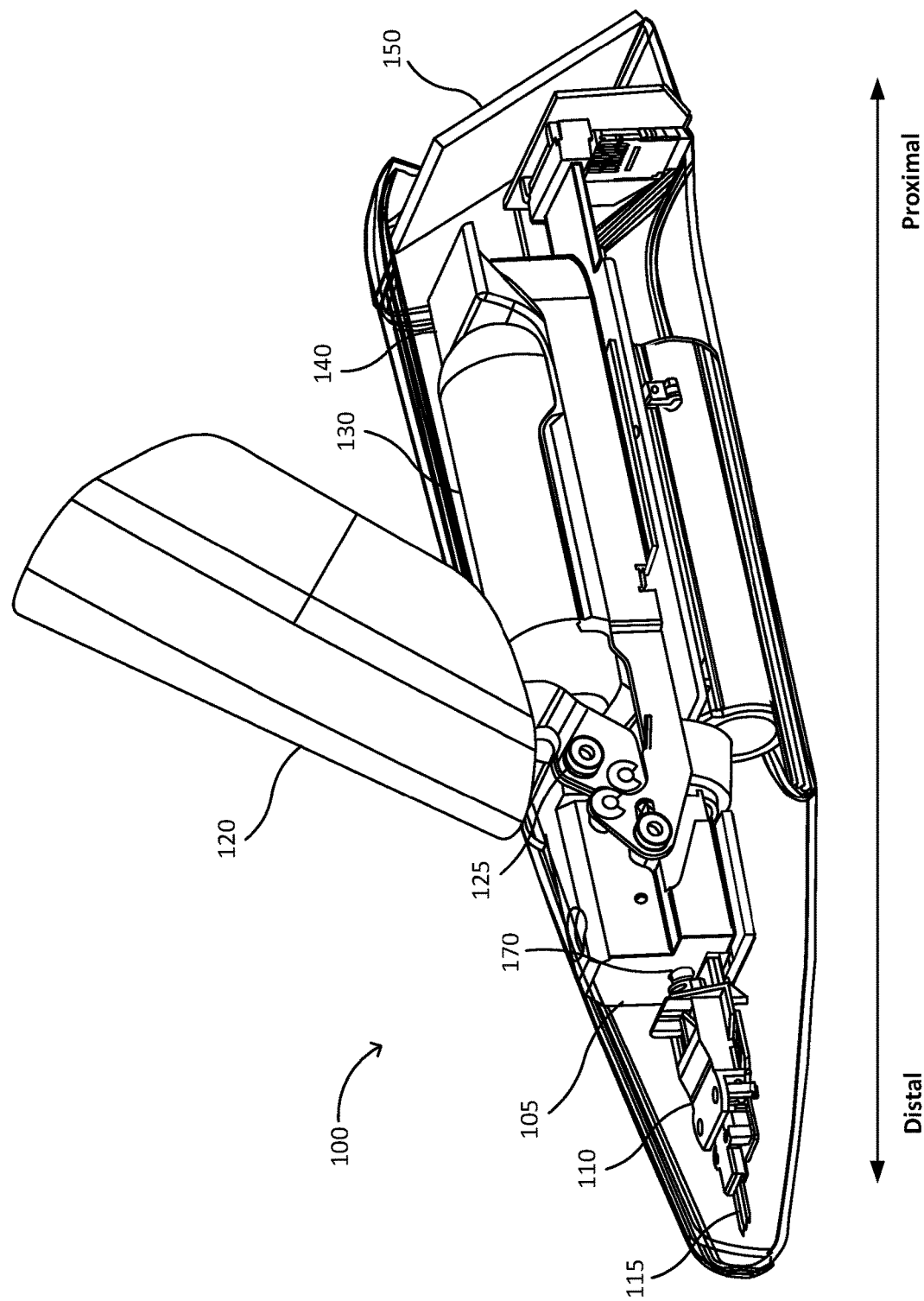
FIGS. 1A-1B illustrate an example embodiment of a cryogenic device including a cartridge holder for holding a cryogen cartridge and a needle probe.
Figure 1B:
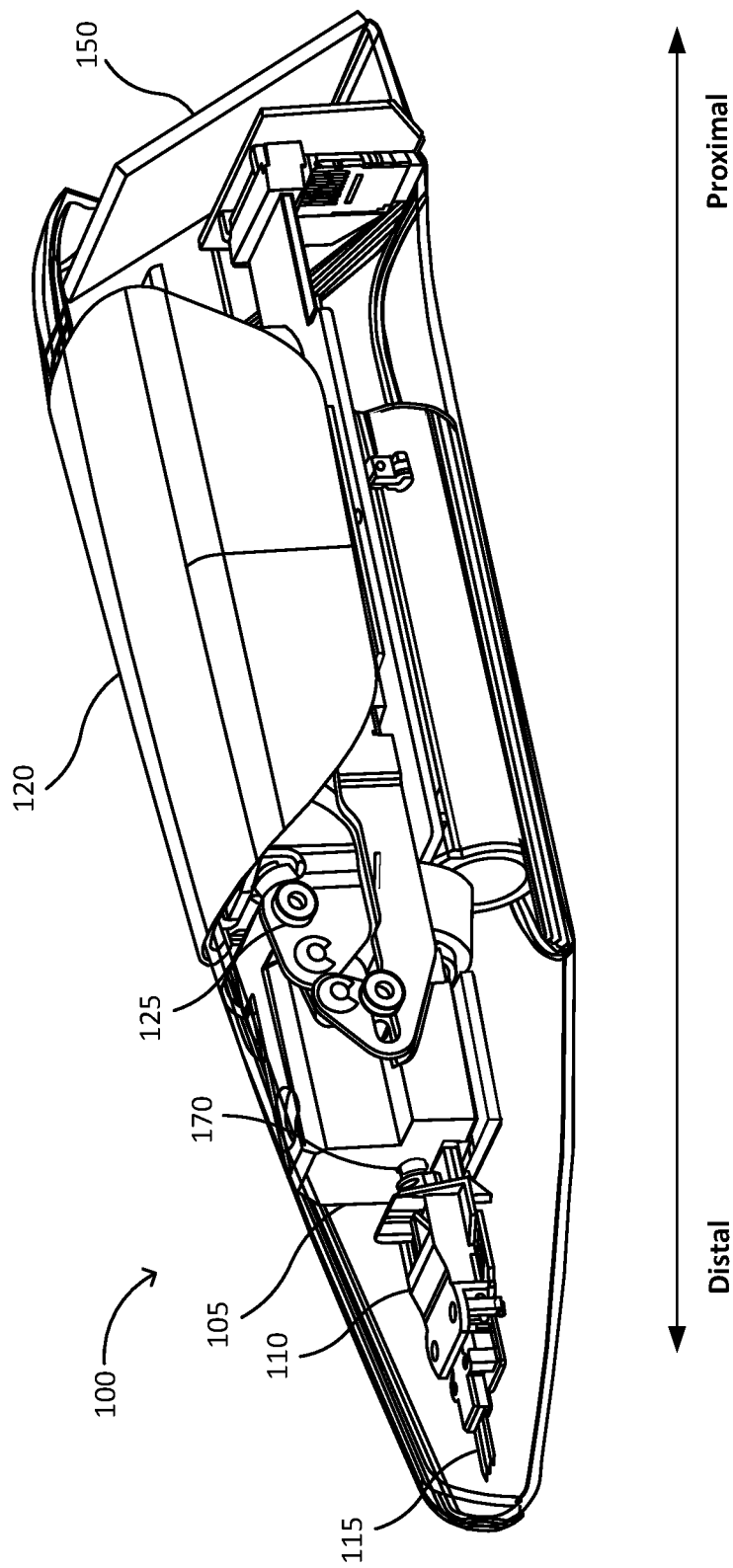

FIGS. 1A-1B illustrate an example embodiment of a cryogenic device 100 including a cartridge holder 140 for holding a cryogen cartridge 130 and a needle probe 110. As shown in the illustrated example embodiment, the cryogenic device 100 may be a self-contained handpiece suitable for being grasped and manipulated by an operator's hand. In other embodiments, the cryogenic device may include physically separated components. For example, the cryogenic device may include a handpiece including a needle probe and a cryogen cartridge that is separated from the handpiece. As will be discussed herein, in some embodiments, the cryogenic device 100 may have a multi-part (e.g., a two-part) housing, with the needle probe 110 disposed within a separate probe housing that may be coupled to a housing of a handpiece portion. In other embodiments, the needle probe 110 may not be disposed within a separate housing and may be configured to be inserted directly into the housing of the cryogenic device 100. As an example, the cryogenic device 100 in at least some of these embodiments may have a single housing. In some embodiments, the cryogen cartridge 130 may be a disposable cartridge filled with a cryogen (e.g., nitrous oxide, fluorocarbon refrigerants, and/or carbon dioxide). In some embodiments, the cryogenic device 100 may include a cartridge door 120 for accessing the cryogen cartridge 130 (e.g., to replace it). The cartridge door 120 may be configured to move from an open position for allowing the cartridge holder 140 to receive a cryogen cartridge 130 to a closed position for securing the cryogen cartridge 130 within the housing of the cryogenic device 100. For example, as illustrated in FIG. 1A-1B, the cartridge door 120 may be configured to swivel around swivel point 125 to allow access to the cryogen cartridge 130. In this example, a user may open the cartridge door 120 (e.g., when the user notices that the cryogen cartridge 130 is empty) as shown in FIG. 1A, remove the cryogen cartridge 130 from the cartridge holder 140, insert a new cryogen cartridge 130 into the cartridge holder 140, and close the cartridge door 120 as shown in FIG. 1B. The described example configuration of the cartridge door 120 and the cartridge holder 140 was designed with user convenience in mind. The cartridge door 120 may be quickly swiveled open with minimal effort and a replacement cryogen cartridge 130 may be inserted with ease. This may be particularly advantageous in cases where an operator has to replace a cryogen cartridge 130 in the middle of a procedure. For example, in some cases, an operator may need to replace a cryogen cartridge 130 in the middle of a treatment cycle after needles 115 of the needle probe 110 have already been inserted into the patient's skin (e.g., in cases where cryogen is depleted during a treatment cycle). In this example, due to the described cartridge door design, the operator may be able to leave the needles 115 in the patient's skin while replacing the cryogen cartridge 130. As a result, the operator is not forced to take the time and effort to reposition the needles 115 at the desired location. Furthermore, the patient is not subjected to further discomfort or unease due to an additional needlestick. In some embodiments, the cartridge holder 140 may allow for an outlet of the cryogen cartridge 130 to protrude through the cartridge holder 140. The outlet may be configured to release the cryogen into a cryogen pathway for allowing the cryogen to pass distally from the cryogen cartridge 130 through the cryogenic device to the desired location (e.g., the needles of the needle probe 110, as discussed below). In some embodiments, the cryogenic device 100 may include a valve between the cryogen cartridge 130 and the cryogen pathway for sealing off the cryogen in the cryogen cartridge 130 from the cryogen pathway (e.g., when a treatment cycle is not occurring).

In some embodiments, as illustrated in FIGS. 1A-1B, the cryogenic device 100 may include a probe receptacle 170 configured to receive a needle probe 110. In some embodiments, the probe receptacle 170 may be configured to couple the needle probe to the cryogen cartridge 130 via the cryogen pathway. In some embodiments, the probe receptacle 170 may be bored into a chassis 105 of the cryogenic device, wherein the chassis 105 includes at least a portion of the cryogen pathway. For example, the chassis 105 may include one or more lumens therein that are coupled to an outlet of the cryogen cartridge 130, and the one or more lumens of the chassis 105 may be coupled to the probe receptacle. In some embodiments, the chassis may include the entire cryogen pathway within the handpiece portion of the cryogenic device 100 (e.g. from the outlet of the cryogen cartridge 130 to the probe receptacle 170). In some embodiments, the chassis 105, or at least the interior surface of the cryogen pathway formed by the chassis 105, may be made of a metal material. The metal material may be configured to reduce the number of nucleation sites and reduce or prevent formation of bubbles from vaporization of the cryogen. As an example, the metal material may be aluminum (or an aluminum alloy). Data has shown that a metal material that includes aluminum may be particularly suitable for reducing or preventing formation of bubbles from vaporization of cryogen (e.g., as the cryogen is flowed along the cryogen pathway), due to the intrinsic properties of aluminum and aluminum alloys. In other embodiments, instead of a metal material, a particular polymer material or a plastic material may be selected based on a determination that the material has a low number of nucleation sites. By reducing the formation of bubbles, it becomes less necessary to prime the cryogenic device 100, thereby reducing the waste of cryogen (and time spent) in priming the device. Experimental data also shows that reducing the length of the cryogen pathway similarly had the effect of reducing the formation of bubbles. As such, the cryogen pathway of the cryogenic device 100 may be of a reduced length, for example, with an optimized device design positioning the cryogen cartridge 130 close to the needle probe 110 and optimized cryogen pathway taking the shortest possible route between the cryogen cartridge 130 and the needle probe 110. In some embodiments, the needle probe 110 may be detachable and/or disposable. In some embodiments, an operator may be able to attach or detach needle probes of different probe types. For example, an operator may attach a first needle probe having a three-needle configuration to perform a first treatment, detach the first needle probe and replace it with a second needle probe having a five-needle configuration.

In the exemplary embodiments illustrated herein, the needle probes are illustrated as having three needles. One of skill in the art will appreciate that the needle probes may have any suitable number of needles (e.g., a single needle, two needles, three needles, four needles, five needles, or more needles). When a plurality of needles are used, they may be arranged in any number of patterns. For example, a single linear array may be used, or a two-dimensional or three-dimensional array may be used. Examples of two-dimensional arrays include any number of rows and columns of needles (e.g. a rectangular array, a square array, elliptical, circular, triangular, etc.), and examples of three-dimensional arrays include those where the needle tips are at different distances from the probe hub 111, such as in an inverted pyramid shape.

Figure 2A:
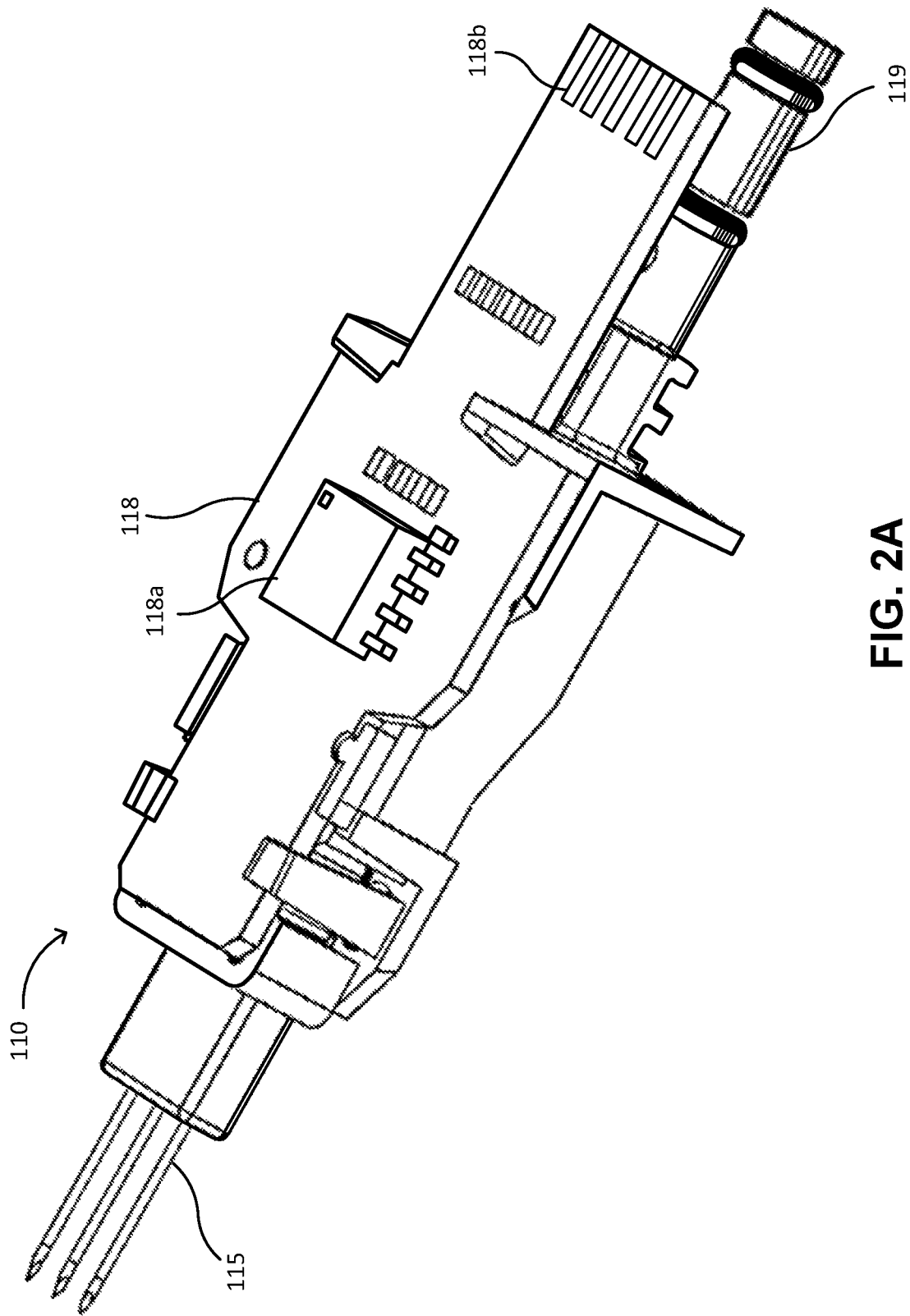
FIG. 2A illustrates an example needle probe.

FIG. 2A illustrates an example needle probe 110. In some embodiments, the illustrated needle probe 110 may have an external housing (not illustrated). In some embodiments, the needle probe 110 may include one or more needles 115 suited for penetration into a patient's skin adjacent to a target tissue (e.g., nerve tissue). For example, as illustrated in FIG. 2A, the needle probe 110 may include three needles 115. Each of the needles of the needle probe 110 may have needle lumens disposed therein (not illustrated). In some embodiments, the needles 115 may have closed tips without any distal openings, such that they do not allow for the ejection of cryogen from the distal end of the needles 115. In these embodiments, the needles 115 themselves are cooled and adjacent target tissue is thereby cooled by conduction. In other embodiments, the needles 115 may have open tips, in which case a target tissue may be cooled by injecting a cryogen into a patient within or adjacent to the target tissue. In some embodiments, the needle probe 110 may include a probe extension 119 that is configured to be securable to the probe receptacle 170. When the needle probe is secured to the probe receptacle 170, the probe extension 119 extends proximally toward the proximal end of the cryogenic device (for illustrative purposes, proximal and distal directions are indicated in FIG. 1A). Referencing FIG. 2A, the probe extension 119 may have a probe lumen (not illustrated) disposed therein, the probe lumen including an elongate element that extends from a proximal end to a distal end. When the needle probe is secured to the probe receptacle, the probe lumen may be fluidically coupled to the cryogen pathway. The probe lumen may also be coupled to the needle lumens of the needles 115 at the distal end of the cryogenic device, such that a cryogen may be allowed to pass through the probe lumen and into the needle lumens (e.g., to cool the needle tips).

In some embodiments, the cryogenic device 100 may be a smart device that includes a first processor (e.g., located within the handpiece and apart from the needle probe 110) to assist the operator with performing a treatment. In some embodiments, the needle probe 110 may be a smart probe. In these embodiments, the needle probe 110 may include a printed circuit board assembly (PCBA). As illustrated in FIG. 2A, the PCBA may include a second processor 118a. In some embodiments, the PCBA may also include a memory component. The PCBA may further include one or more connectors 118b (e.g., a card edge connector) that electrically couple the needle probe 110 to the remainder of the cryogenic device 100 (e.g., the handpiece portion). For example, when a needle probe is received by the probe receptacle 170, a portion of the PCBA 118 (including the connectors 118b) may be received by a port in the handpiece portion. FIGS. 2B-2C illustrate an example embodiment of a port 178 of a PCBA 175 of the handpiece portion receiving the proximal portion of a PCBA 118 of the needle probe 110. As illustrated in the example embodiment of FIGS. 2B-2C, the connectors 118b of the PCBA 118 may be configured to slide into an opening of the port 178 of the PCBA 175 of the handpiece portion.

Once the PCBA 118 of the needle probe 110 is connected to the PCBA 175 of the handpiece portion, the needle probe 110 may be able to transmit and/or receive information to/from the handpiece portion (e.g., via the second processor 118a). In some embodiments, the needle probe 110 may transmit a probe descriptor that may, among other things, identify a corresponding probe type of the needle probe. For example, the probe descriptor may identify the number of needles (e.g., a single-needle probe, a three-needle probe, a five-needle probe), the lengths of needles, the configuration of needles (e.g., a rectangular array, a square array, elliptical, circular, triangular, a three-dimensional shape such as an inverted pyramid shape), or any other suitable characteristics of the needle probe. In these embodiments, the first processor may be further configured to determine, based on the received probe descriptor information, that the detachable needle probe is of a particular probe type of a plurality of probe types. In some embodiments, the probe descriptor information may include information about the needle probe 110 that may be used to derive treatment-related information. For example, the probe descriptor information may include an average cryogen flow rate for an associated probe, which may be used by the first processor (e.g., on the handpiece) to calculate an amount of cryogen that has been used and/or an amount that is remaining in the cryogen cartridge 130. The first processor may calculate these amounts based on the average cryogen flow rate and the amount of time a supply valve for releasing cryogen has been opened. As another example, needle dimensions, the number of needles, and other suitable parameters associated with the needle probe 110 may be used to derive cryogen flow amounts, cryogen amount used during a cycle, a cryogen amount remaining in a cartridge, and/or any other suitable treatment-related information. As another example, the probe descriptor information may include information that may be used by other treatment functionalities such as a skin warmer (e.g., a resistive heating element that is configured to be near or adjacent to the skin during treatment) that is configured to apply heat energy to a skin surface to reduce or prevent collateral tissue damage. In this example, a particular probe may send probe descriptor information that may be used to determine parameters for operating the skin warmer (e.g., power level, duration of heating, etc.). More information about cryogenic devices with skin warmers may be found in U.S. Pat. No. 10,470,813 filed Mar. 14, 2016, which is incorporated herein by reference in its entirety for all purposes. This information may be shown on a display (e.g., in real-time as a treatment is being performed) associated with the cryogenic device 100 (e.g., referencing FIG. 5, displayed on the LCD screen 150). In some embodiments, a treatment recommendation may be determined and shown on the display. For example, a particular needle probe 110 may be associated with a particular type of treatment, and a treatment recommendation may thus be displayed based on a determination that the particular needle probe 110 has been inserted. An operator may then perform a treatment based on this recommendation. In some embodiments, the probe descriptor information may include "expiration" details of the needle probe 110 (e.g., the needle probe 110 may be configured to expire after a set number of treatment cycles for safety reasons). More information about smart cryogenic devices and smart tips may be found in U.S. Pat. No. 10,130,409 filed Nov. 20, 2018, which is incorporated by reference herein in its entirety for all purposes.

In some embodiments, the first processor may receive any other suitable information (e.g., from one or more sensors associated with the cryogen cartridge 130), such as the amount of cryogen remaining (or at least the available useful cryogen) within the cryogen cartridge 130 once the cryogen cartridge 130 is positioned in the cartridge holder 140. This information may be stored, transmitted, and/or displayed at a suitable location (e.g., referencing FIG. 5, displayed on the LCD screen 150).

The needle probes may be secured to the probe receptacle 170 via any suitable means. For example, a needle probe 110 and the probe receptacle 170 may be threaded such that the needle probe 110 may be screwed into the probe receptacle 170. Such a "screw-type" connection mechanism has the advantage of being secure even under high pressures exerted by cryogen on the needle probe 110 as the cryogen flows into the needle probe 110. However, some operators may find such a mechanism inconvenient in some cases, because screwing needle probes into and out of probe receptacles may be cumbersome and time-consuming. The time and effort required to replace needle probes may in some cases translate into significant costs over time, as the number of procedures that an operator can perform effectively may be reduced. This issue may be particularly exacerbated in cases where an operator needs to switch between needle probes in the middle of a procedure.

Figure 2D:
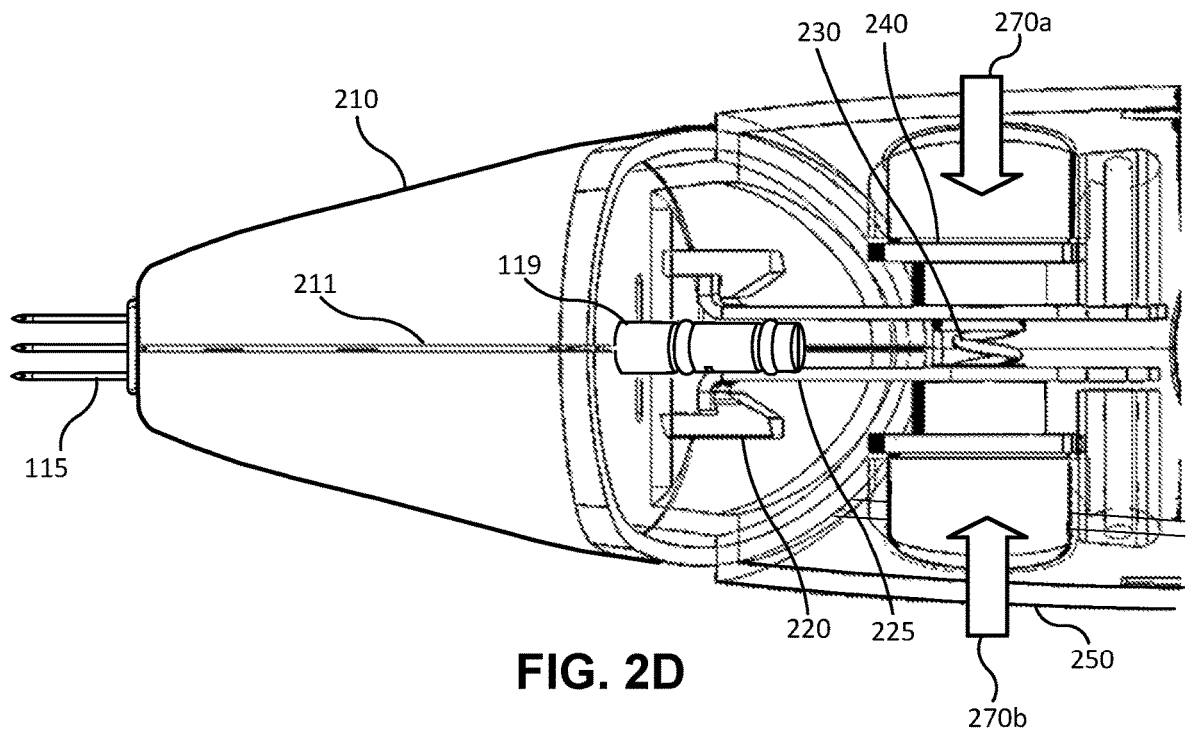

At least in part to address the above-mentioned issues, "quick-connect" mechanisms were developed for quickly connecting and disconnecting needle probes. FIGS. 2D-2I illustrate example embodiments of quick-connect mechanisms for quick connection and/or disconnection of needle probes 110 from a handpiece portion 250 of a cryogenic device 100. In some embodiments, needle probes 110 may be coupled to (e.g., and disposed within) a probe housing 210, as illustrated in FIG. 2D. FIG. 2D shows a probe housing 210 and a cross-section of a handpiece portion 250. In the example embodiment of FIG. 2D, a needle probe (the entirety of which is not visible) having needles 115 and probe extension 119 is disposed within the probe housing 210. In FIG. 2D, a needle lumen 211 is shown extending from the probe extension 119 toward the needles 115 (it is to be understood that the needle lumen 211 in FIG. 2D is disposed within the probe housing 210, but the needle lumen 211 is exposed in FIG. 2D for illustrative purposes). FIG. 2D illustrates a first example of a quick-connect mechanism. The probe housing 210 may include one or more probe snaps 220 (e.g., the two probe snaps 220 illustrated in FIG. 2D), which may be protruding elements configured to engage with one or more handpiece clips 225 (e.g., the two handpiece clips 225 illustrated in FIG. 2D) of the handpiece portion 250. As illustrated, the probe snaps 220 may include a retaining portion that is configured to mate with or otherwise engage a corresponding retaining portion of the handpiece clips 225 and thereby secure the probe snaps 220 (and thereby securing the probe housing 210). In some embodiments, a handpiece clip 225 may include an elongate portion and a first retaining portion at an end of the elongate portion, and a probe snap 220 may include an elongate portion and a second retaining portion (e.g., at an end of its elongate portion) configured to engage the first retaining portion. In some embodiments, the handpiece clips 225 may be biased toward an engaging position configured to engage with and retain the probe snaps 220 (as illustrated in FIG. 2D) by an elastic element 230 (e.g., a spring). The handpiece clips 225 may be moved toward a disengaging position by moving one or more input elements 240. For example, as illustrated in FIG. 2D, two input elements 240 may be coupled to two handpiece clips 225 on opposite sides. In this example, each of the input elements 240 may be moved, for example, in the respective directions depicted by the arrows 270a and 270b in FIG. 2D, compressing the elastic element 230 and thereby displacing the handpiece clips 225 toward each other to cause the handpiece clips 225 to be in the disengaging position. For example, a user may depress one or more buttons associated on an exterior of the handpiece portion 250 to cause the input element 240 to move. The one or more buttons in this example may be discrete elements coupled to the input elements 240, or may be part of the input elements 240 that extend to the exterior of the handpiece portion 250. This displacement disengages the handpiece clips 225 from the probe snaps 220, and thereby releases the probe housing 210 from the handpiece portion 250. The handpiece clips 225 may be brought back to the engaging position when the elastic element 230 is no longer compressed by the input elements 240 (e.g., when a user releases one or more associated buttons on an exterior of the handpiece portion that are coupled to the input elements 240). Although FIG. 2D illustrates only two handpiece clips 225, input elements 240, and probe snaps 220, the disclosure contemplates any suitable number of such elements.

Figure 2E:
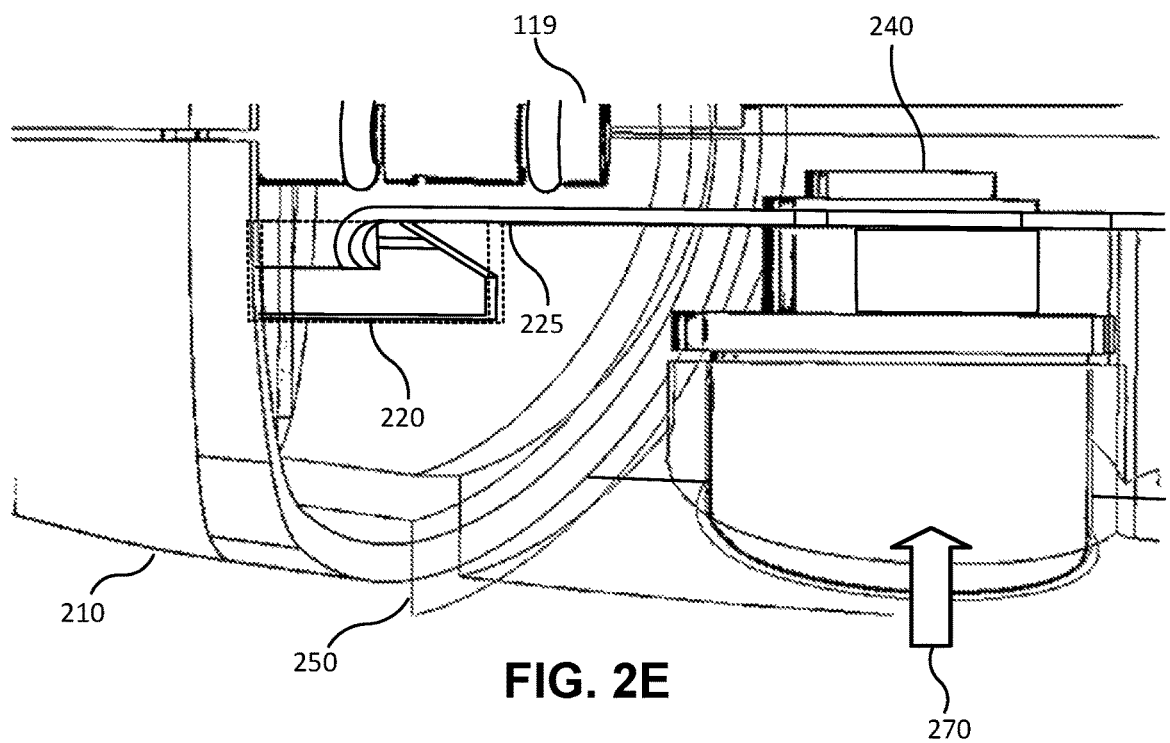

FIG. 2E illustrates another example of a quick-connect mechanism. In some embodiments, a handpiece clip 225 may be formed and coupled (e.g., directly fastened) to a handpiece portion 250 such that it is naturally biased toward an engaging position configured to engage a probe snap 220 as illustrated in FIG. 2E. For example, the handpiece clip 225 may be an elastic element such as a flat spring configured to have an element of shape memory. Flat springs may be manufactured from, for example, high carbon spring steel, nickel-silver, high-nickel alloys, stainless steel, phosphor-bronze, beryllium-copper combinations, a suitable plastic material, or any other suitable material. The handpiece clip 225 illustrated in FIG. 2E may be coupled to the handpiece portion 250 and coupled to the input element 240, such that the input element 240 is configured to cantilever the handpiece clip 225. As described above the input element 240 may be coupled to one or more buttons on an exterior of the handpiece portion 250 (alternatively, the input element 240 may have an exterior part that extends to the exterior of the handpiece portion 250 such that the exterior part functions as the button). By moving the input element 240 (e.g., by pushing a corresponding button in the direction depicted by the arrow 270 in FIG. 2E), the handpiece clip 225 may be temporarily displaced toward a disengaging position. This displacement disengages the handpiece clip 225 from the probe snap 220, and thereby releases the probe housing 210 from the handpiece portion 250. The handpiece clip 225 may be brought back to the engaging position when input element 240 is no longer being pushed in the direction depicted by the arrow 270 in FIG. 2E (e.g., when a user releases an associated button on an exterior of the handpiece portion). Although FIG. 2E illustrates only one handpiece clip 225, input element 240, and probe snap 220, the disclosure contemplates any suitable number of such elements (e.g., two input elements 240 on opposing sides, two corresponding handpiece clips 225 coupled to the handpiece portion 250, and two corresponding probe snaps 220).

FIG. 2F illustrates another example of a quick-connect mechanism. In some embodiments, a connected handpiece clip 226 with one or more prongs (e.g., the two prongs illustrated in FIG. 2F) may be used to retain a probe housing 210. The connected handpiece clip 226 may be naturally biased toward an engaging position configured to engage a probe snap 220 as illustrated in FIG. 2F. For example, the connected handpiece clip 226 may be a single flat spring. The handpiece clip 226 may be coupled to the input element 240, such that moving the input elements 240 (e.g., in the direction illustrated in FIG. 2F) displaces the handpiece clip 226 toward a disengaging position, disengaging the handpiece clip 226 from the probe snap 220, and thereby releasing the probe housing 210 from the handpiece portion 250. Although FIG. 2F illustrates only one probe snap 220 and one input element 240, the disclosure contemplates that any number of such elements (e.g., another input element 240 and another corresponding probe snap 220 configured to engage the opposing prong of the handpiece clip 226 illustrated in FIG. 2F) may be employed.

FIG. 2G illustrates another example of a quick-connect mechanism. In some embodiments, a handpiece clip 225 may be coupled to an input element 240 configured to slide (e.g., as illustrated by the double-sided arrow 270 in FIG. 2G) between a first location (e.g., at a proximal point) and a second location (e.g., at a distal point), such that sliding the input element 240 moves the handpiece clip 225 between an engaging position and a disengaging position. In the example illustrated in FIG. 2G, the handpiece clip 225 is in an engaging position that engages the probe snap 220. The handpiece clip 225 may be configured to be deflected (e.g., in the direction indicated by the arrow 275) when the input element 240 is moved in the proximal direction (e.g., to the right of the figure) toward a proximal point as it pivots around the input element 240 and the bearing surface 260. In doing so, the handpiece clip 225 may be caused to be in a disengaging position that disengages the handpiece clip 225 from the probe snap 220, thereby releasing the probe housing 210 from the handpiece portion 250. Also in this example, the handpiece clip 225 may be configured to be returned back to the engaging position by moving the input element 240 in the distal direction (e.g., to the left of the figure) toward a distal point. Alternatively or additionally, the handpiece clip 225 may be an elastic element such as a flat spring that is biased such that the handpiece clip 225 may be configured to return back to the engaging position when the input element 240 is released. Alternatively or additionally, a separate spring element (e.g., in communication with the input element 240 or the handpiece clip 225) may be used to push the handpiece clip 225 to the engaging position. Although FIG. 2G illustrates only one probe snap 220 and one input element 240, the disclosure contemplates that any number of such elements (e.g., another input element 240 and another corresponding probe snap 220 configured to be on opposing side of the handpiece portion 250).

Figure 2H:
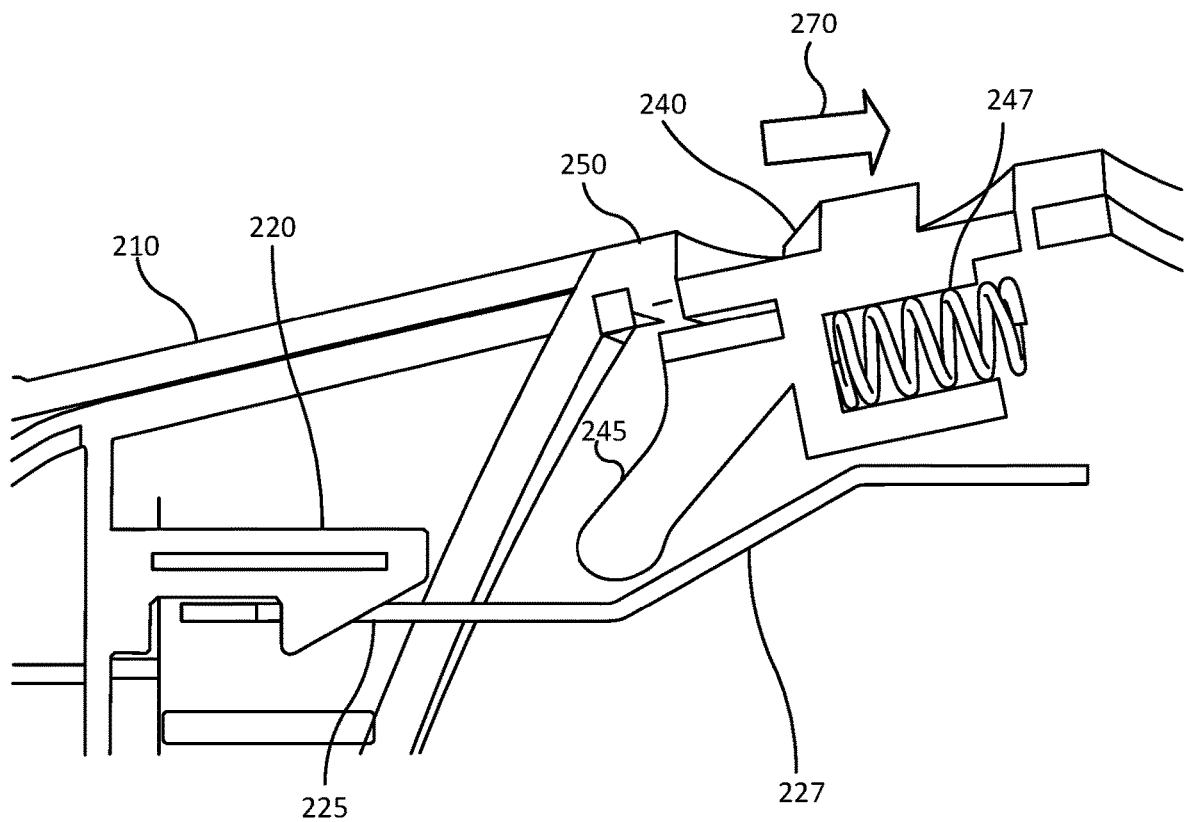
Figure 2I:
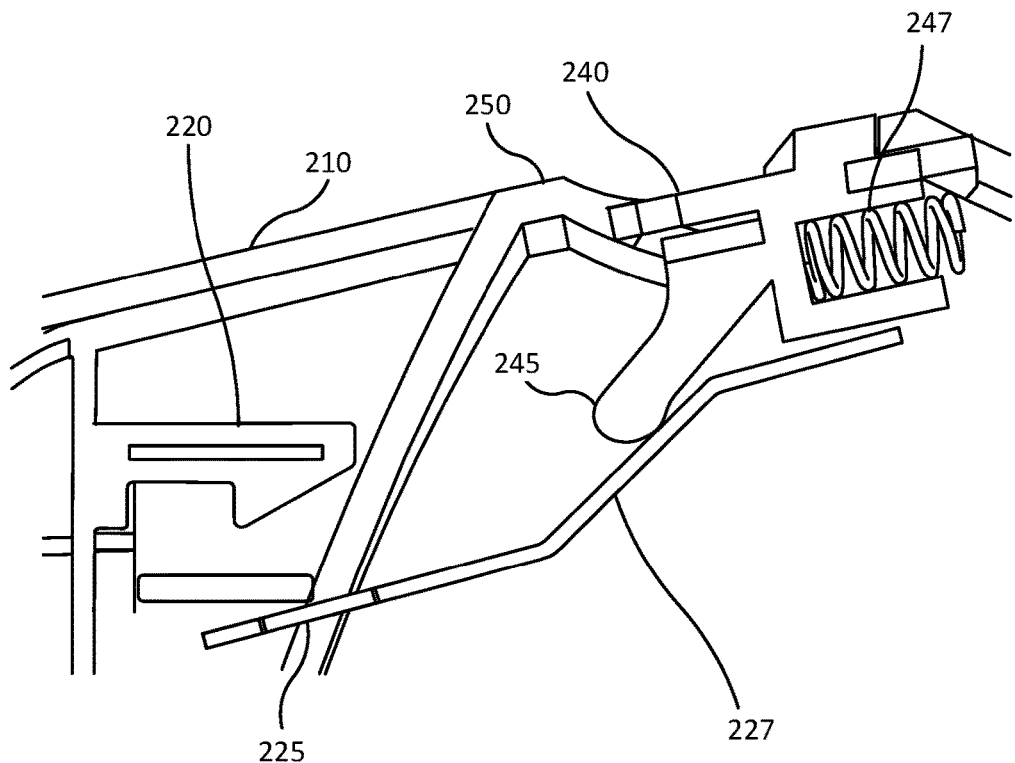

FIGS. 2H-2I illustrate another example of a quick-connect mechanism. In this example, the input element 240 and corresponding extension 245 may be actuated to cause the handpiece clip 225 to move between an engaging position and a disengaging position. FIG. 2H illustrates the handpiece clip 225 in the engaging position. The handpiece clip 225 may be an elastic, resilient element (e.g., a flat spring) that is biased toward the engaging position, such that it latches onto the probe snap 220, thereby helping secure the probe housing 210 to the handpiece portion 250. The handpiece clip 225 may be moved to a disengaging position by actuating the input element 240 (e.g., when a user slides the input element 240 in a proximal direction as illustrated by the arrow 270 in FIG. 2H). The disengaging position is illustrated in FIG. 2I. As illustrated in FIG. 2I, when the input element 240 is actuated proximally, the extension 245 pushes against the angled portion 227 of the handpiece clip 225, causing a distal portion of the handpiece clip 225 to deflect down and away from the probe snap 220. This may disengage the handpiece clip 225 from the probe snap 220, and thereby release the probe housing 210 from the handpiece portion 250. In some embodiments, as illustrated in FIGS. 2H-2I, the quick-connect mechanism may include a spring element 247 that is compressed when the input element 240 is in a proximal position (when the handpiece clip 225 is in the disengaging position) as illustrated in FIG. 2I. Thus, when the input element 240 is released, the spring element 247 is configured to return the actuator to the engaging position (e.g., the position illustrated in FIG. 2H). Although FIGS. 2H-2I illustrate only one probe snap 220 and one input element 240, the disclosure contemplates that any number of such elements (e.g., another input element 240 and another corresponding probe snap 220 configured to be on an opposing side of the handpiece portion 250).

Figure 2J:
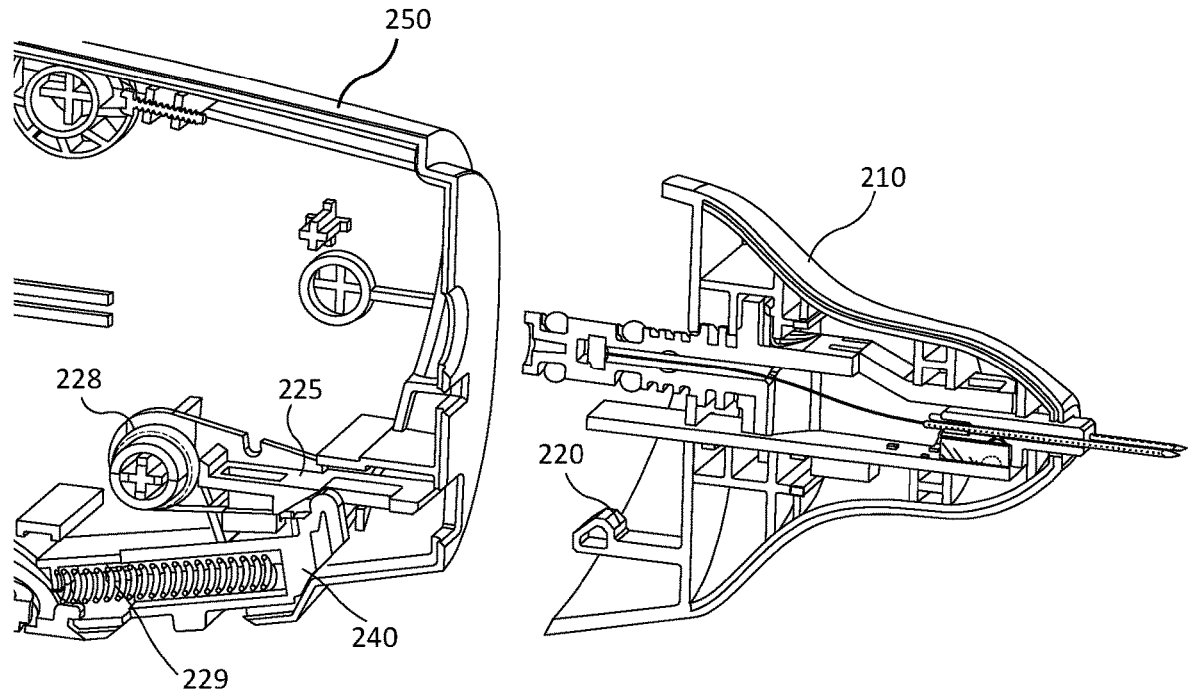
FIGS. 2J-2M illustrate additional embodiments of quick-connect mechanisms for quick connection and/or disconnection of needle probes from a handpiece portion of a cryogenic device.
Figure 2K:
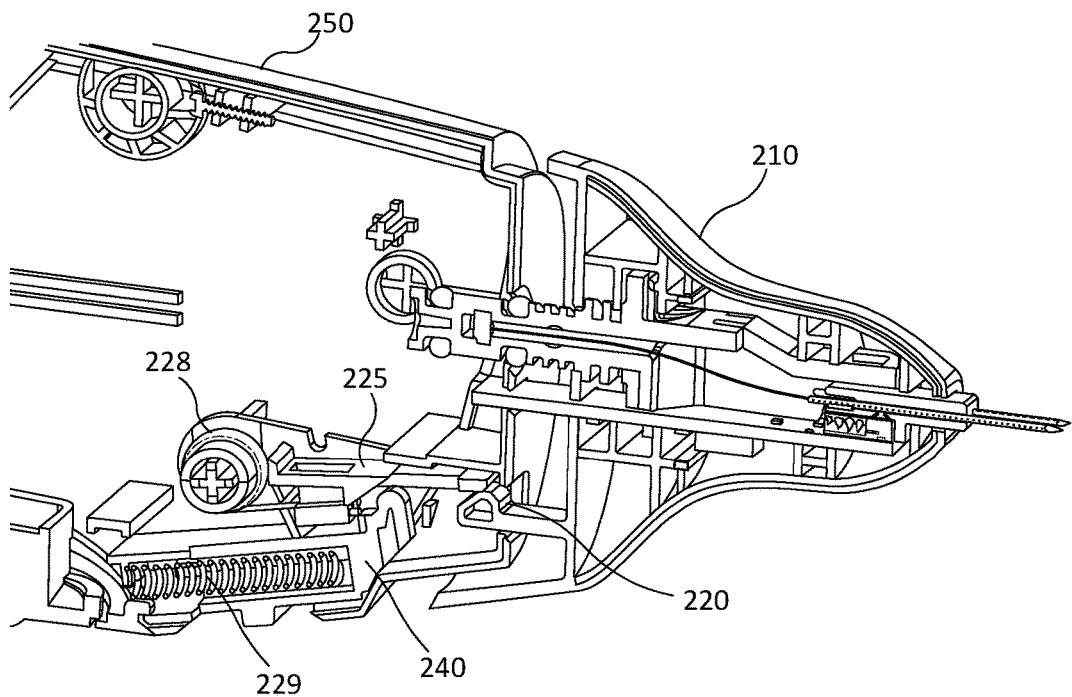
Figure 2L:
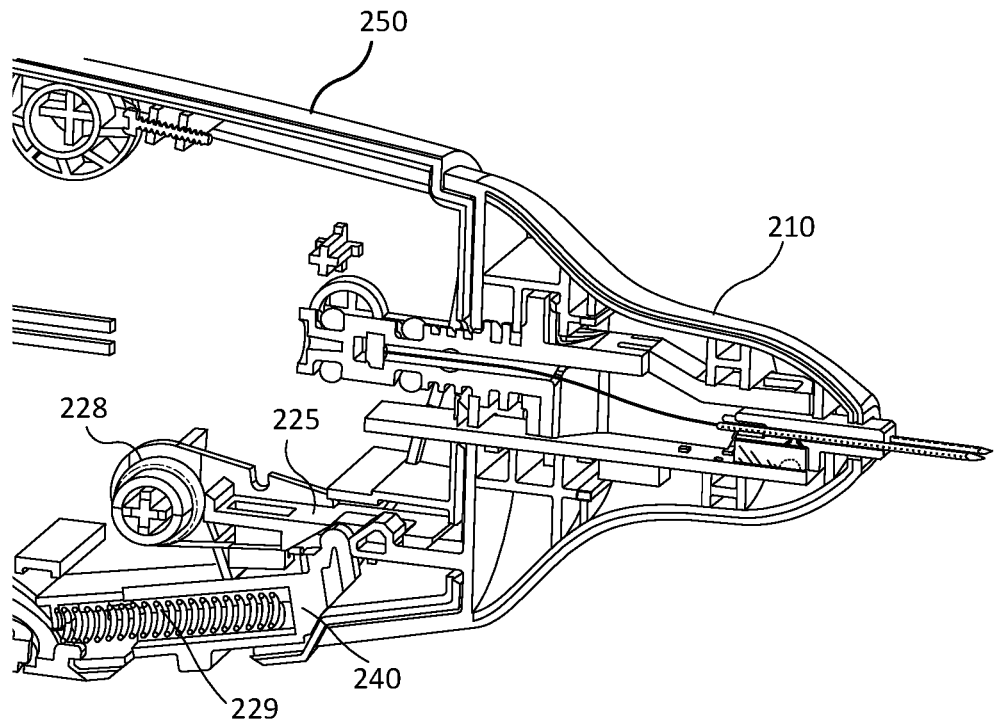
Figure 2M:
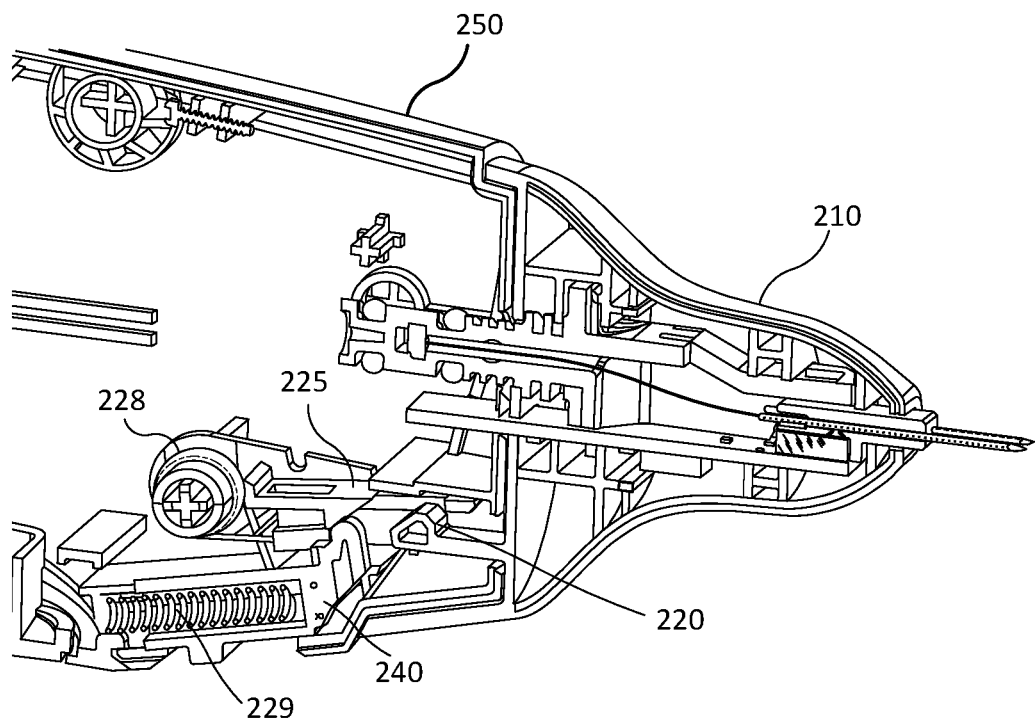

FIGS. 2J-JM illustrate additional embodiments of quick-connect mechanisms for quick connection and/or disconnection of needle probes from a handpiece portion of a cryogenic device. In this example, the handpiece clip 225 may comprise a latch element formed of a rigid plastic or metal material that is biased toward the engaging position by a separate torsion spring 228. The latch element 225 pivots on support elements in the handpiece enclosures, such that it latches onto a hook feature of the probe snap 220, thereby helping secure the probe housing 210 to the handpiece portion 250 as shown in FIGS. 2K and 2L. FIG. 2M illustrates probe tip detachment when the input element 240 comprising a sliding element, detach button, or other release actuator is retracted to allow disconnection of the probe housing 210. In this embodiment, the release actuator 240 reacts against a ramp feature in the latch element 225 such that retracting the release actuator via the compression spring 229 causes the latch element 225 to rotate slightly counter clock wise as illustrated (or clockwise) so as to release the latch from the hook feature of the probe snap 220 of the probe needle housing 210. The handpiece clip 225 may then be configured to return back to the engaging position when the input element 240 is released as shown in FIG. 2J, where the torsion spring 228 returns the latch to its biased engaging position. This latch 225 design with separate torsion spring 228 provides for a more reliable and robust quick-connect mechanism as the functions are separated into two separate parts.

In the various example quick-connect mechanisms described herein, a probe housing 210 (e.g., a probe housing 210 including a replacement needle probe) may be locked into a handpiece portion 250 simply by pushing its probe snaps 220 against the distal portion of the handpiece clips 225 until the probe snaps 220 snap into place. The probe snaps may be configured to deform so as to be able to move beyond the barriers effectuated by retaining portions of the handpiece clips 225. As illustrated in FIGS. 2D-2I, in some embodiments, the proximal end of the probe snaps 220 may be angled so as to facilitate this maneuver. Alternatively, in some embodiments, the probe snaps 220 may only be able to move beyond the protrusions of the handpiece clips 225 when the handpiece clips 225 are maintained in the disengaging position (e.g., using the input elements 240). Although the examples of FIGS. 2D-2I illustrate particular mating configurations, with one or more snaps (e.g., the probe snaps 220 illustrated in these figures) in the probe housing 210 and one or more elongated handpiece clips (e.g., the handpiece clips 225 illustrated in these figures) in the handpiece portion 250, the disclosure contemplates any suitable mating configuration with any suitable mating features. For example, elongated clips may be included in the probe housing 210 and snaps may be included in the handpiece portion 250. As another example, a combination mating configuration may be employed, with clips and snaps on both the probe housing in the handpiece portion.

In some embodiments, a needle probe 110 itself (in addition to or as an alternative to the probe housing 210) may be snap-fit into a probe receptacle 170 via one or more corresponding grooves and protrusions that may be present on the surface of the needle probe 110 and the probe receptacle 170. For example, an operator may select a first needle probe 110 of a first type and push the probe extension 119 of the first needle probe 110 into the probe receptacle 170 until the first needle probe 110 snaps into place. In this example, the operator may at some point choose to detach the first needle probe 110 (e.g., to replace the first needle probe with a second needle probe 110, or to simply dispose of the first needle probe 110), at which point the operator may pull the needle probe 110 until it snaps out of the probe receptacle 170. In some embodiments, alternatively or additionally, a needle probe may be secured to a probe receptacle via a movable protrusion mechanism (e.g., a spring latch in the probe receptacle that is configured to bolt into associated corresponding recesses in the needle probe, or alternatively, a spring latch in the needle probe that is configured to bolt into associated corresponding recesses in the probe receptacle). For example, an operator may select a first needle probe 110 of a first type and push a portion of the first needle probe 110 (e.g., the probe extension 119) into the probe receptacle 170. This may cause a spring latch within the probe receptacle 170 to be actuated to an "open" position to allow the first needle probe 110 to move beyond a threshold point, after which the spring latch may clamp down into a recess in the first needle probe 110. Alternatively, the spring latch may be moved to the "open" position when the operator performs a suitable input (e.g., actuating a button). In these examples, the operator may later detach the first needle probe 110 by, for example, performing a suitable input such as actuating a button. In some embodiments, rather than a latch that is configured to bolt into a recess, the cryogenic device may employ any other suitable retention mechanism (e.g., a clamp mechanism that retains a needle probe 110 by applying force radially inward against the probe extension 119).

The quick-connect mechanisms have the added advantage over screw-type connection mechanisms in that quick-connect mechanisms may reduce the number of circuit boards or circuit board elements (e.g., flex circuitry) necessary to enable smart-probe functionality. A screw-type connection mechanism requires the needle probe to rotate with respect to the handpiece portion. As such, a circuit board of the needle probe cannot simply be inserted into a port of the handpiece portion (unlike, for example, the embodiment illustrated in FIGS. 2B-2C, where the PCBA 118 is simply inserted into the port 178). Instead, a device with a screw-type connection mechanism would need to accommodate the rotation by means of additional circuitry (e.g., a stationary connector mechanism that is perpendicular to the planes of the PCBAs, and one or more flex circuitry elements). Since the quick-connect mechanisms do not require rotational movements, as illustrated in FIGS. 2B-2C, a single PCBA 118 of a needle probe 110 can be simply inserted into the port 178 of the handpiece portion. Such a configuration not only has the effect of reducing manufacturing costs, but it also reduces the likelihood of device malfunctions (e.g., because of fewer parts in motion, and because of fewer parts in general).

FIG. 3A illustrates a cross-section schematic of a configuration for coupling a lumen of an example needle probe 110 to a cryogen pathway of a cryogenic device. Initial testing involved a configuration similar to that of the schematic illustrated in FIG. 3A with a quick-connect mechanism as described above. In the illustrated configuration, a probe extension 119 of a probe tip 110 is configured to be inserted into a probe receptacle 170. The needle probe 110 may include one or more needles (e.g., the plurality of needles 115 illustrated in FIG. 3A) at a distal end that emanate from the probe head 111, with the probe head 111 being coupled to the probe extension 119. The probe receptacle 170 may couple the needle probe 110 to the cryogen pathway, with a supply valve 122 in between a cryogen inlet 123 (through which cryogen from the cryogen cartridge flows) and the needle probe 110, as illustrated by the arrows in FIG. 3A. Testing of the quick-connect mechanism with the configuration illustrated in FIG. 3A showed that the high pressure within the cryogenic device presented technical challenges. Specifically, the flow of cryogen through the cryogen pathway and into the needle probe 110 is at extremely high pressures. As the cryogenic flows into the probe lumen, this high pressure exerts a significant linear force in the distal direction. Even securing the needle probe 110 using one or more O-rings (e.g., the O-rings 117a and 117b, whose cross-sections are shown in FIG. 3A) was not adequate. FIG. 3B is a close-up view of the O-ring 117a of FIG. 3A from a different perspective. While these O-rings provided radially compressive forces that helped mitigate the linear force of the cryogen, they were not sufficient for stabilizing the needle probe 110 within the probe receptacle 170. Without a screw mechanism securing the needle probe 110, the needle probe 110 was prone to being ejected out of the probe receptacle 170. In an attempt to solve this problem, a design with robust retaining latches for securing the needle probe 110 was developed, but this design proved to be technically challenging. For example, the small geometries involved (e.g., as may be necessitated in the case of a handheld device) require tight tolerances in latch-mechanism dimensions to ensure that the probe does not move when it is under pressure. Manufacturing a device with such tight tolerances may be technically challenging, expensive, and may generally be difficult to accomplish in large-scale production.

Figure 3C:
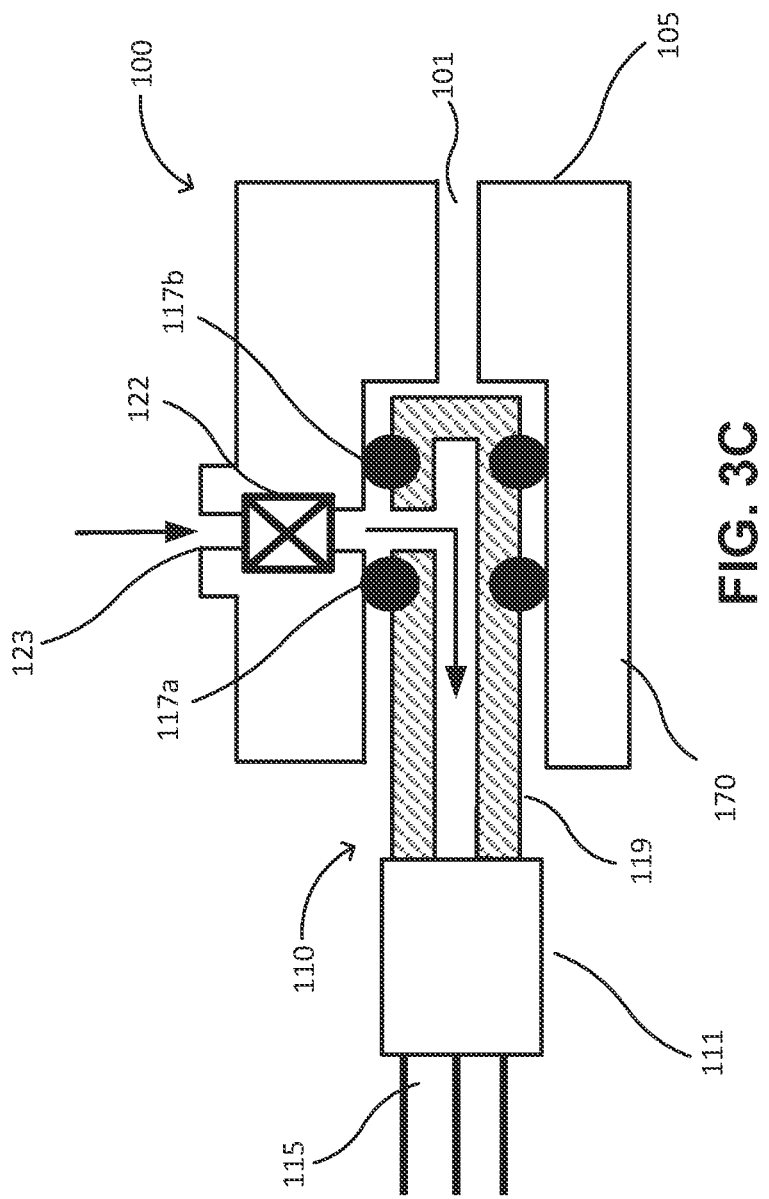
FIG. 3C illustrates a cross-section schematic of a novel configuration for coupling a lumen of a needle probe to a cryogen pathway.

FIG. 3C illustrates a cross-section schematic of a novel configuration for coupling a lumen of a needle probe 110 to a cryogen pathway. The illustrated configuration reduces or eliminates the outward forces (e.g., linear forces with a vector extending distally from the probe receptacle 170) exerted by the cryogen on the needle probe 110. In some embodiments, the needle probe 110 may be configured such that the lumen of the needle probe 110 couples to the cryogen pathway at a first location that is deliberately placed at a point in between the proximal end and the distal end of the needle probe 110. As illustrated by the arrows, the path taken by the flow of cryogen is altered. In the illustrated configuration of FIG. 3C, the high-pressure forces exerted by the cryogen as it flows past the valve 122 and into the needle probe 110 no longer creates a significant outward force. Instead, the forces are distributed radially around the perimeter of the needle probe 110, and the resulting forces in the distal and proximal directions are balanced, resulting in no (or insignificant) net force in the distal direction. As such, the needle probe 110 is no longer prone to be ejected or destabilized by the flow of cryogen into the needle probe 110, and this was experimentally confirmed. Unlike the configuration illustrated in FIG. 3A, in the configuration illustrated in FIG. 3C, the proximal end of the needle probe 110 is exposed to relatively low pressures (e.g., ambient air) and does not experience the high pressures generated by the cryogen flow. The result is that pressure at the proximal end (e.g., ambient air pressure) and at the distal end (e.g., ambient air pressure) of the needle probe 110 may be equalized or substantially equalized, and there is thus no substantial outward force generated by the cryogen as it enters the needle probe 110. In some embodiments, the one or more sealing elements such as O-rings may be placed within the probe receptacle 170 to seal the probe receptacle (e.g., from the cryogen as it is allowed to flow into the needle probe 110). For example, as illustrated in FIG. 3C, O-rings 117a and 117b may be placed on either side of the first location at which the lumen of the needle probe 110 couples to the cryogen pathway. In this example, the O-rings 117a and 117b may seal the probe receptacle 170 at the proximal and distal sides of the first location to cause the cryogen to enter the lumen of the needle probe 110 without leaking past the O-rings 117a and 117b and, for example, venting into ambient air. In some embodiments, the O-rings or other suitable sealing elements may serve to further stabilize the needle probe 110. For example, placing the O-rings 117a and 117b as illustrated in FIG. 3C (on either side of the first location) serves to stabilize the needle probe 110, and this was confirmed by experimental data. In some embodiments, as illustrated in FIG. 3C, the cryogenic device 100 may include a passageway 101 at the proximal end of the needle probe 110. The passageway 101 may be configured to allow egress of cryogen if, for example, a sealing element (e.g., the O-ring 117b) failed. Such a mechanism may be a failsafe mechanism that allows for the safe release of cryogen in a proximal direction away from the patient, thereby reducing the risk of high-pressure buildup from excess cryogen.

Figure 4A:
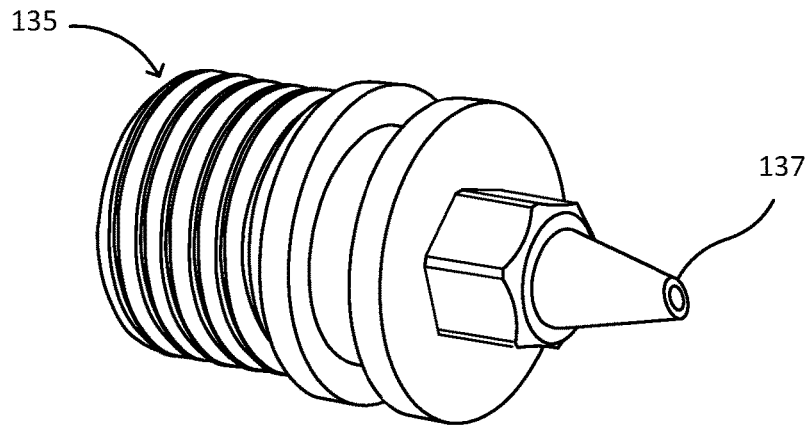
FIGS. 4A-4B illustrate a piercing element that may be used to pierce a cryogen cartridge.
Figure 4B:
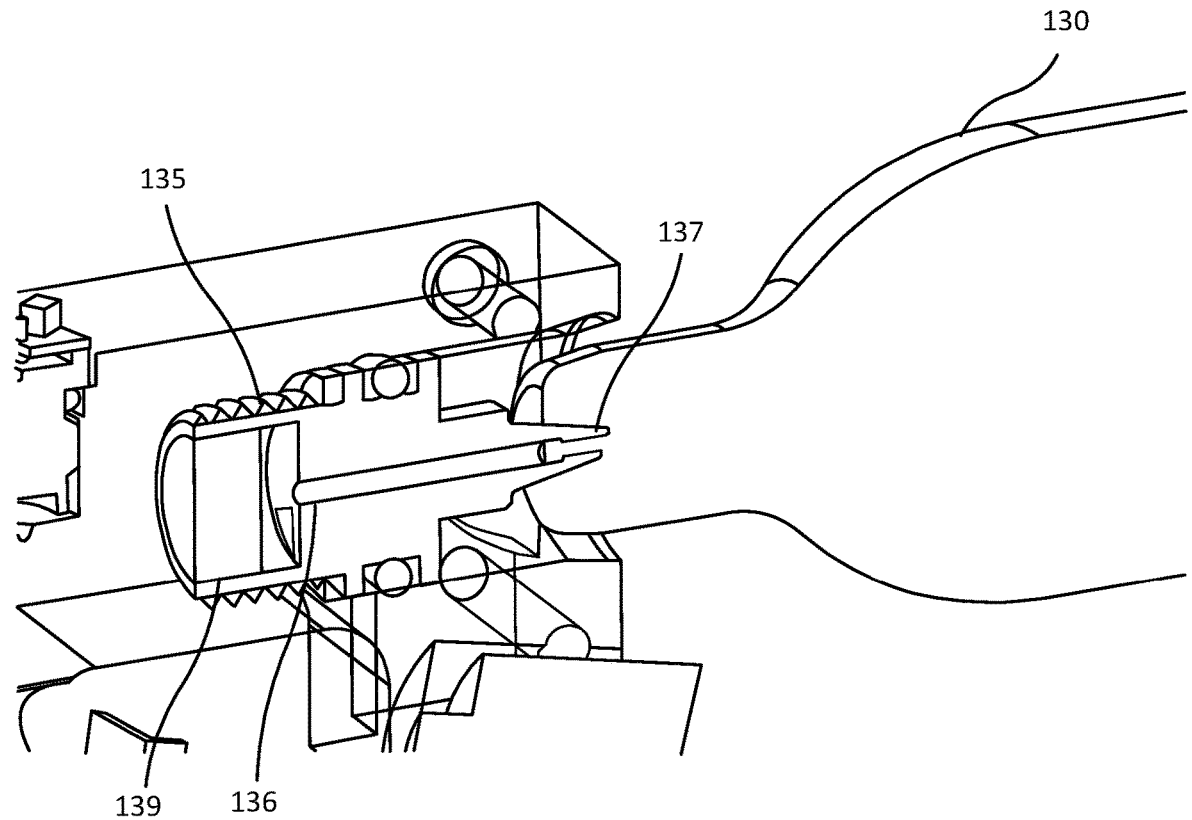

FIGS. 4A-4B illustrate a piercing element 135 that may be used to pierce a cryogen cartridge 130. In some embodiments, the piercing element 135 may be housed within the cryogenic device, in a position so as to pierce the cryogen cartridge 130 using the piercing point 137. In some embodiments, the piercing element 135 may pierce the cryogen cartridge 130 without further input once the cryogen cartridge 130 is locked into place. For example, the act of positioning the cryogen cartridge 130 within the cartridge holder 140 and closing the cartridge door 120 may cause the cryogen cartridge 130 to be pierced. In this example, closing the cartridge door 120 may cause the cryogen cartridge 130 to move toward (e.g., translate laterally with respect to) the piercing element 135 (or vice versa), thereby causing the cryogen cartridge 130 to be pierced. This example mechanism is advantageous in that it greatly facilitates the process of inserting a cryogen cartridge 130 and getting the cryogenic device 100 to a "ready" state quickly—not only does it integrate the cartridge positioning/locking and piercing into one step, it allows the cartridge door to be a lever that provides mechanical advantage for piercing the cryogen cartridge 130. In other embodiments, the piercing element 135 may only pierce the cryogen cartridge 130 after receiving a further input (e.g., following actuation of a button that causes the piercing element 135 to slide toward the cryogen cartridge 130, or one that causes the cryogen cartridge 130 to slide toward the piercing element 135). Once the cryogen cartridge 130 is pierced, the cryogen within may be fluidically coupled to the cryogen pathway via a pathway 136 that extends through the piercing element 135. In some embodiments, one or more valves (e.g., referencing FIG. 3C, the supply valve 122) may be disposed at a distal point along the cryogen pathway to allow for control of cryogen flow.

Figure 5:
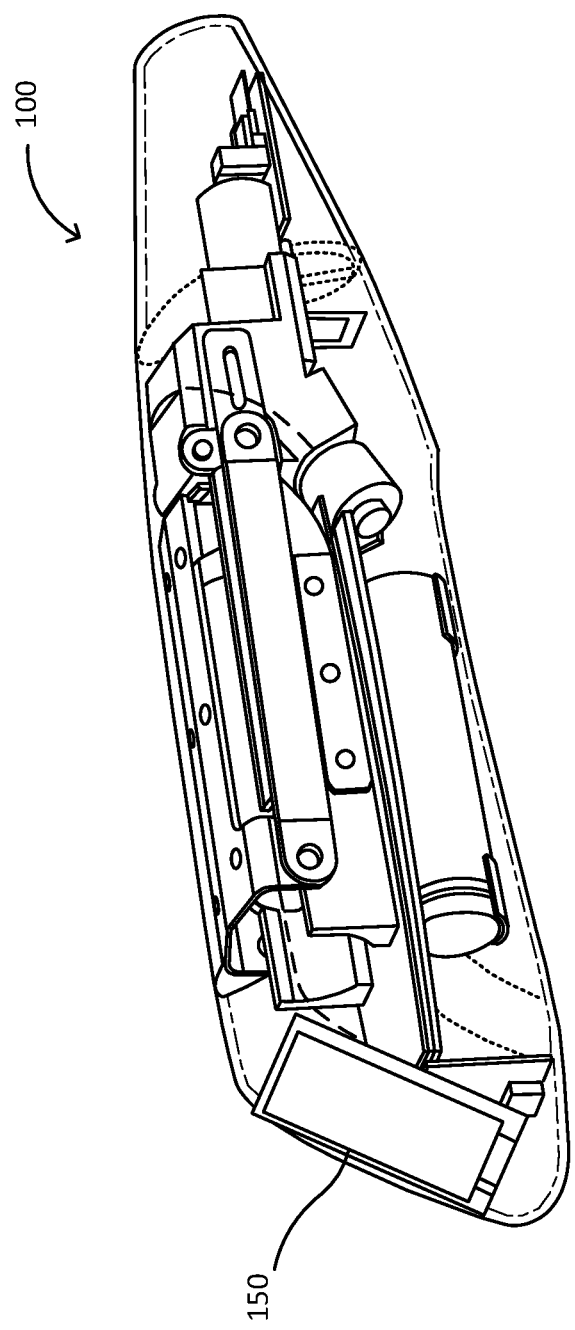
FIG. 5 illustrates a cryogenic device having an LCD display.

FIG. 5 illustrates a cryogenic device 100 having an LCD display 150. In some embodiments, the LCD display 150 may provide a user interface that is capable of displaying a variety of useful information to the operator before, during, and/or after treatment. For example, the LCD display 150 may present information about a needle probe 110 that is currently positioned within the probe receptacle 170 (e.g., information derived from a probe descriptor received from the needle probe 110, as described above).

Figure 6A:
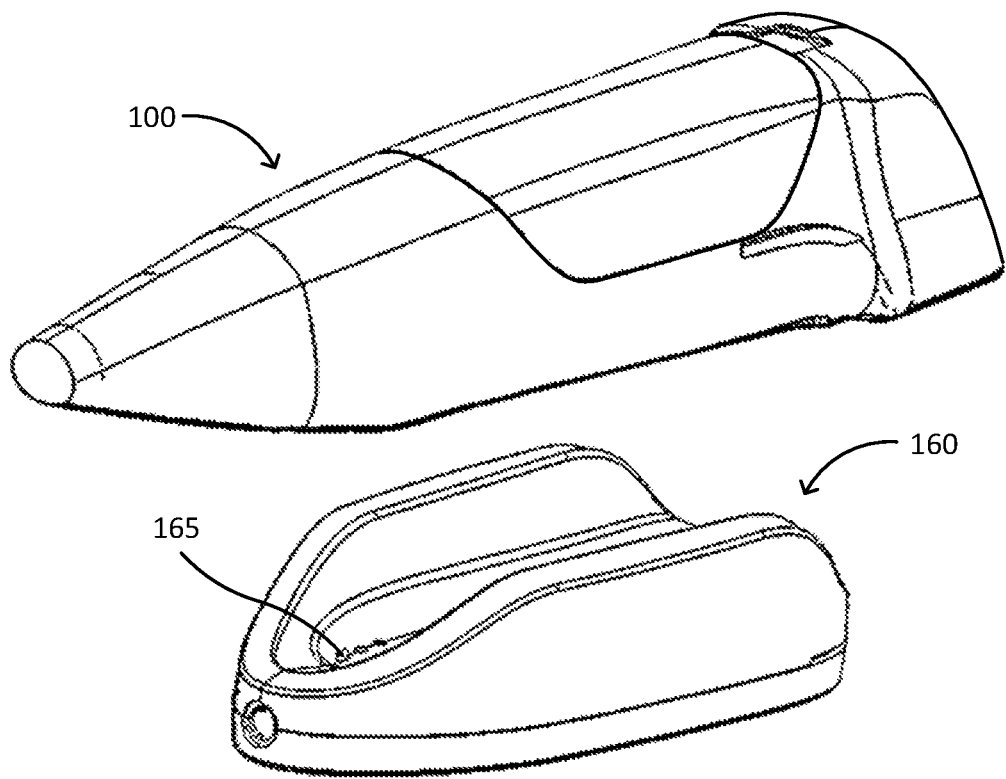
FIGS. 6A-6B illustrate an example embodiment of a cryogenic device being docked onto a charging device.
Figure 6B:
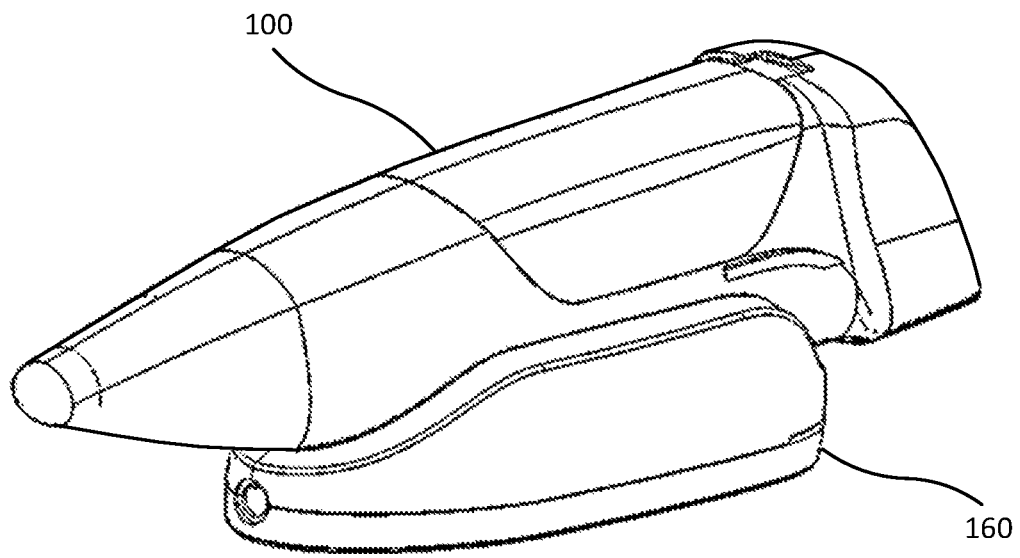

In some embodiments, the cryogenic device 100 may be rechargeable. For example, the cryogenic device 100 may include one or more rechargeable batteries that may be recharged by coupling the cryogenic device 100 to a charging device. FIGS. 6A-6B illustrate an example embodiment of a cryogenic device 100 being docked onto a charging device 160. As illustrated in FIG. 6A, the charging device 160 may include one or more connectors 165 capable of being coupled to corresponding connectors (not illustrated) along the external housing of the cryogenic device 100. As illustrated in FIG. 6B, the charging device 160 and the cryogenic device 100 may be shaped such that the cryogenic device 100 is adapted for being docked onto the charging device 160, which may charge the cryogenic device 100. In the illustrated example, the handpiece portion of the cryogenic device 100 is configured to rest substantially horizontally (or along an axis along which the cryogenic device extends) on a charging cradle to receive charging energy from the charging cradle. The charging device 160 may be configured to be plugged into an electrical source. Alternatively or additionally, the charging device 160 may itself include one or more batteries that may be used to supply energy to the cryogenic device 100. In some embodiments, the charging device 160 may be a wireless charger, and the cryogenic device 100 may be charged wirelessly when it is within range. In some embodiments, the charging device 160 may be a smart charger that is capable of communicating with the cryogenic device 100. Communication between the cryogenic device 100 and the charging device 160 may be via electrical contacts, a direct optical connection, or a wireless connection (e.g., Bluetooth, wireless LAN). In some embodiments, the charging device 160 may be configured to receive information from the cryogenic device 100, connect to a network (e.g., via local WIFI, wired LAN, cellular networks), and transmit the received information (or a modified version of the received information) to an external device (e.g., a smartphone, a desktop computer, a remote server device). In some embodiments, the charging device 160 may be configured to transmit the received information (or a modified version of the received information) to an external device such as a smart phone or a desktop computer via a wired or wireless connection. For example, the charging device 160 may transmit such information to a smart phone vial a Bluetooth connection.

In some embodiments, the cryogenic device 100 may include one or more filtration devices (e.g., referencing FIG. 4B, the filter 139 within the handpiece portion of the cryogenic device 100, which may be within the piercing element 135 as illustrated) along the cryogen pathway for filtering out impurities in the cryogen. These impurities may have been introduced to the cryogen during manufacturing, as a result of puncturing the cartridge to access the refrigerant, or from the environment in which the cryogenic device 100 is used. Solid impurities can compromise the performance of the cryogenic device by occluding passageways and/or creating leak paths in sealing mechanisms. Fluid impurities, both liquids and gasses, such as oil, water, oxygen, nitrogen, and carbon dioxide can also be present within the cryogen cartridge. These impurities may also occlude or restrict cryogen pathways, and/or chemically alter properties of the refrigerant. The filtration device may include an element for capturing solids, as well as or alternatively an element for capturing fluids. The filtration device may include any suitable combination of particulate filters and/or molecular filters. More information about filters in cryogenic devices may be found in U.S. Pat. No. 9,155,584 filed Jan. 14, 2013, which is incorporated by reference herein in its entirety for all purposes. In some embodiments, the filter 139 may be replaceable (e.g., by replacing the piercing element 135, or by simply replacing the filter 139).

Figure 7A:
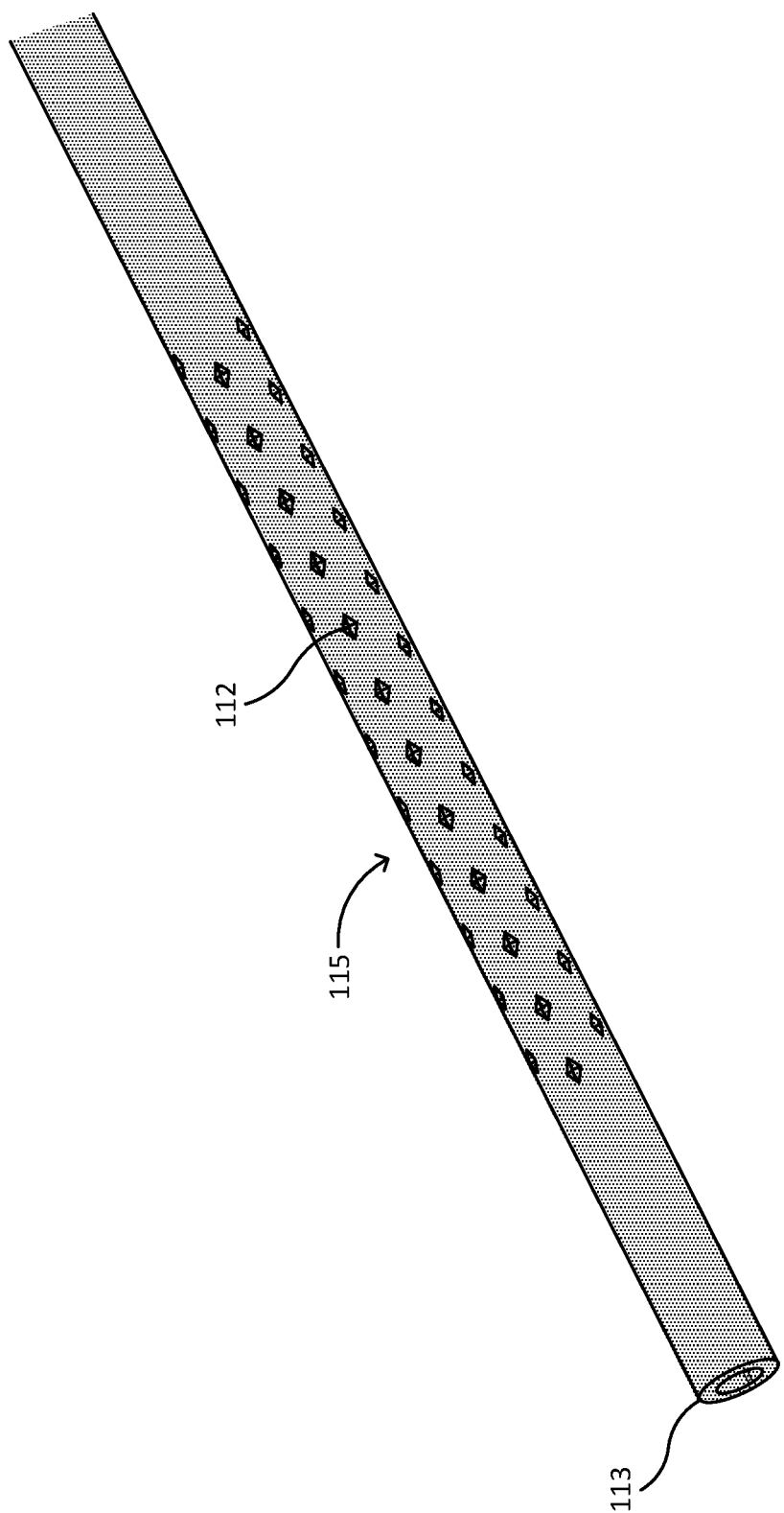
FIGS. 7A-7C illustrate close-up images of example embodiments of a needle (e.g., a needle included in a needle probe) having a plurality of echogenic markers.
Figure 7C:
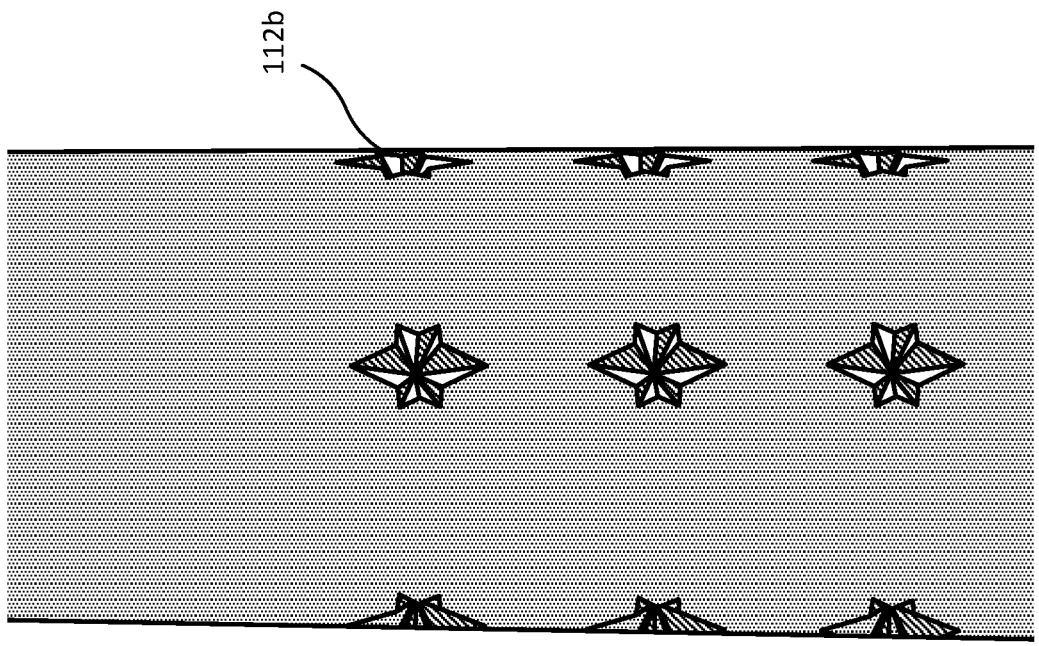
Figure 7B:
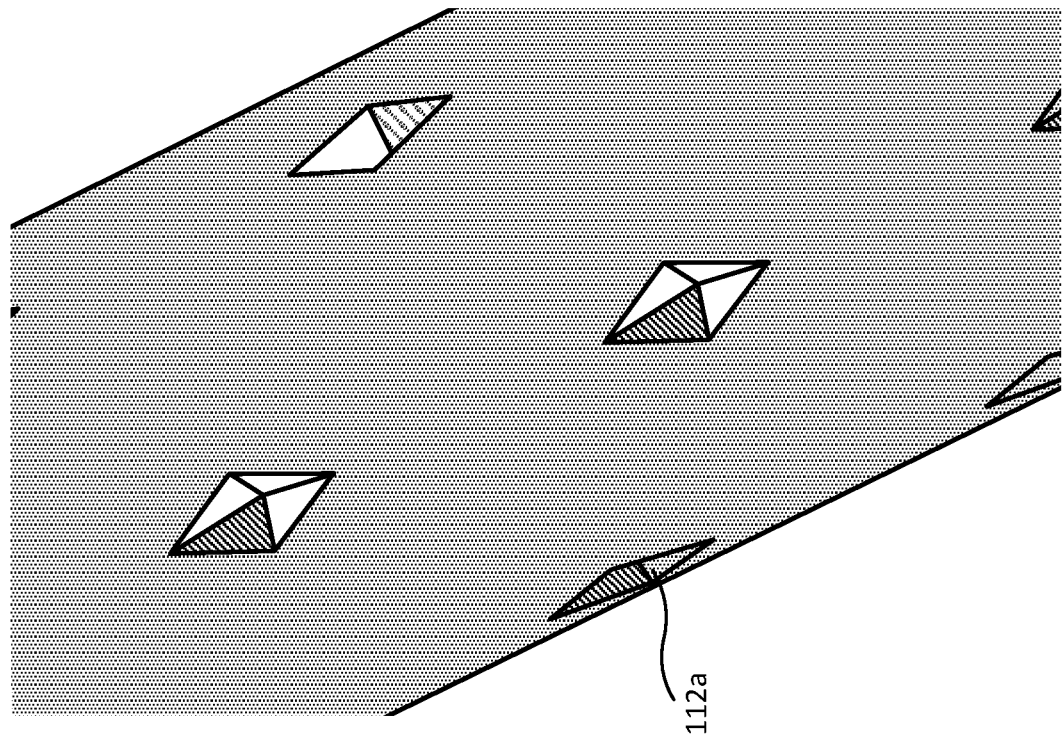

FIGS. 7A-7C illustrate close-up images of example embodiments of a needle (e.g., a needle 115 included in a needle probe 110) having a plurality of echogenic markers 112. The echogenic markers 112 may extend along a length of the needle 115, and may extend around the circumference of the needle. The echogenic markers 112 may be designed so as to have high echogenicity (e.g., the ability to bounce an echo or return an ultrasonic signal in ultrasound examinations). These echogenic markers 112 may make the needle 115 more visible using ultrasound. FIG. 7A illustrates a portion of the needle 115, showing a proximal opening 113 leading to a needle lumen within the needle 115. In some embodiments, the echogenic markers 112 may be depressions made along a surface of the needle 115. As an example, the echogenic markers 112 may be depressions having around 0.002 inches in depth. In other embodiments, the echogenic markers 112 may be projections that protrude from the surface of the needle 115. In some embodiments, echogenic markers 112 may be incorporated onto the needles 115 of the needle probes 110 to allow an operator to visualize the needles and thereby aid the operator in positioning the needles 115 at a desired location (e.g., adjacent to a target tissue). In some embodiments, the echogenic markers may have designs (e.g., polygonal designs) having sharp corners that may be particularly suitable in some cases for detection using ultrasound. For example, some or all of the designs may be of a polygonal design that are of a diamond shape or a star shape, or a polygonal design that includes a diamond shape or a star shape. FIGS. 7B and 7C illustrate example designs, showing that the echogenic markers 112 may be diamond-shaped (e.g., referencing FIG. 7B, the echogenic marker 112a) or star-shaped (e.g., referencing FIG. 7C, the echogenic marker 112b). In some embodiments, the echogenic markers 112 may be used to identify a location at which a cryozone is expected to be formed around the needles 115. For example, a subset of the echogenic markers 112 may be specially marked (e.g., having a different design from the remainder of the echogenic markers 112), indicating to an operator that a cryozone is expected to form around the subset. Any suitable manufacturing technique may be used to create the echogenic markers 112. For example, echogenic markers 112 may be created using machining techniques, laser cutting, laser etching, and/or controlled punching/stamping.

Figure 8:
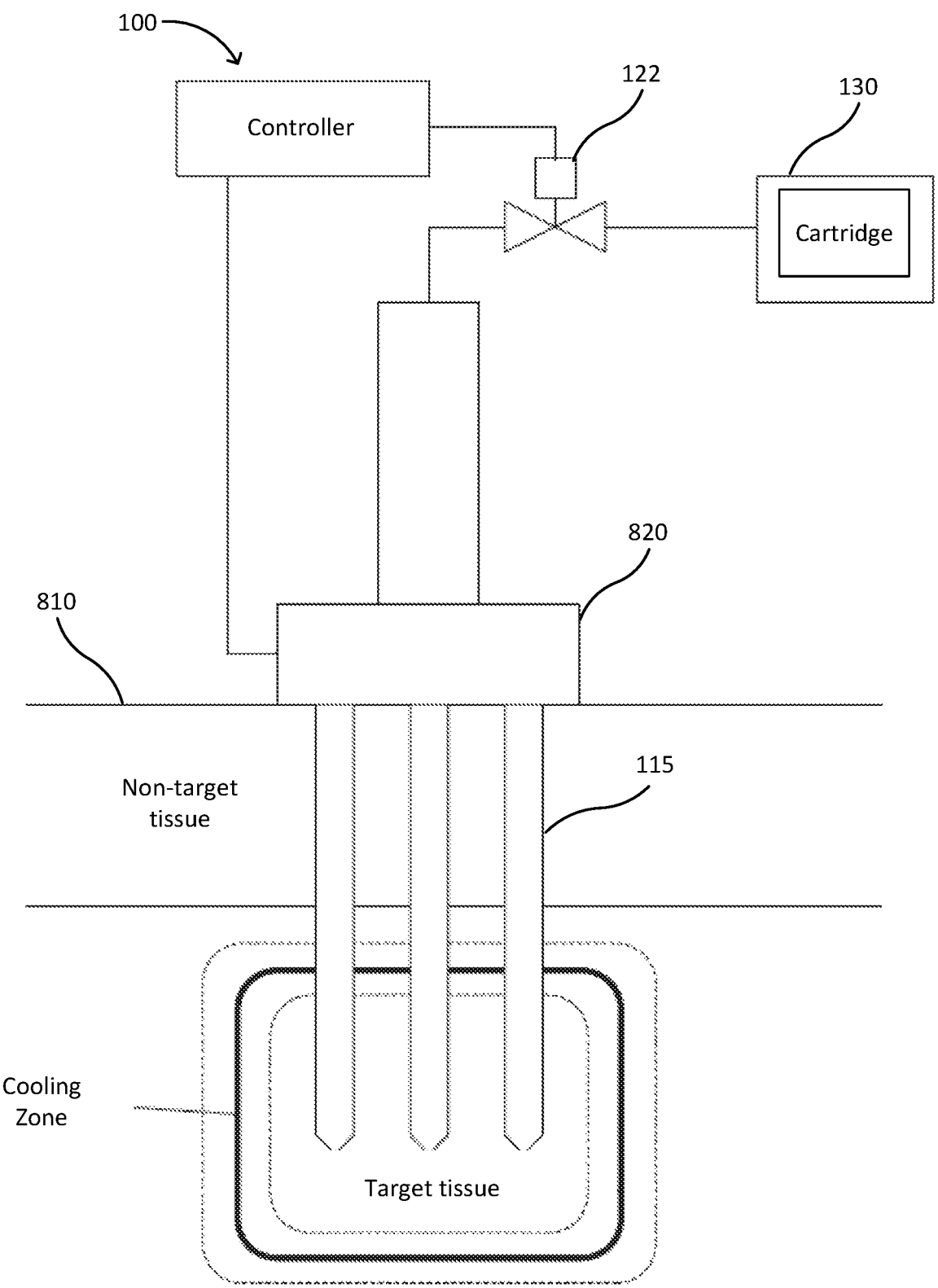
FIG. 8 illustrates a simplified schematic diagram of a cryogenic device while in use.

FIG. 8 illustrates a simplified schematic diagram of a cryogenic device 100 while in use. As illustrated, the needles 115 may be inserted into and beyond the skin 810 of the patient such that distal portions of the needles 115 are adjacent to a target tissue (e.g., nerve tissue). In some embodiments, an operator may select a needle probe such that the needles 115 are sized so as to extend distally beyond non-target tissue and adjacent to a target tissue when a tissue-engaging surface 820 is made to contact the skin 810. In some embodiments, once the needles 115 are positioned, an operator may submit an input to the cryogenic device 100 (e.g., by actuating a button, tapping a user interface element on a touchscreen, etc.) to cause a controller to open a supply valve 122, thereby enabling a cryogen to flow from the cartridge 130 to the lumens of the needles 115 via a cryogen pathway. The needles 115 may be configured such that distal portions of the needles 115 are cooled more than proximal portions of the needles 115. As such, the distal portions of the needles 115 may create a cooling zone around the target tissue as illustrated in FIG. 8.

Figure 9:
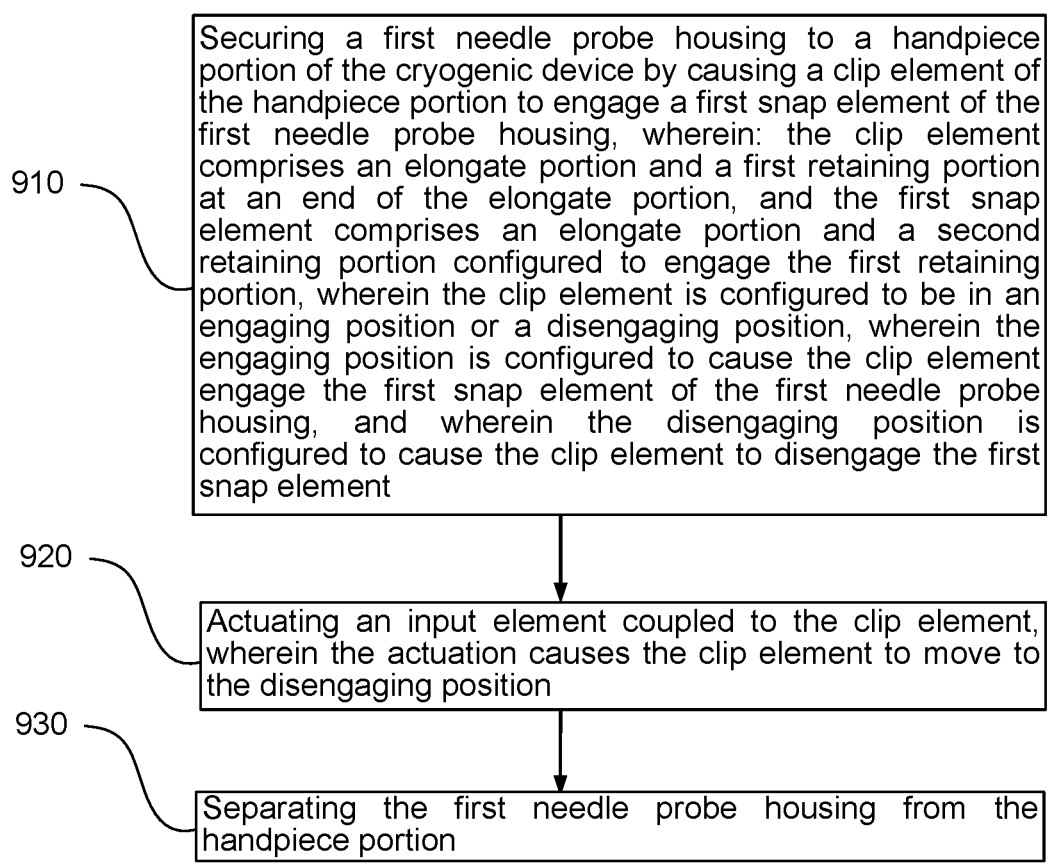
FIG. 9 illustrates an example method for replacing a needle probe in a cryogenic device.

FIG. 9 illustrates an example method 900 for replacing a needle probe in a cryogenic device. The method may begin at step 910, where a first needle probe housing secured to a handpiece portion of a cryogenic device by causing a clip element of the handpiece portion to engage a first snap element of the first needle probe housing. The clip element may include an elongate portion and a first retaining portion at an end of the elongate portion, and the first snap element may include an elongate portion and a second retaining portion configured to engage the first retaining portion. The clip element may be is configured to be in an engaging position or a disengaging position, wherein the engaging position is configured to cause the clip element to engage the first snap element of the first needle probe housing, and wherein the disengaging position is configured to cause the clip element to disengage the first snap element. At step 920, an input element coupled to the clip element may be actuated, wherein the actuation causes the clip element to move to the disengaging position. At step 930, the first needle probe housing may be separated from the handpiece portion. Particular embodiments may repeat one or more steps of the method of FIG. 9, where appropriate. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates an example method for replacing a needle probe in a cryogenic device, including the particular steps of the method of FIG. 9, this disclosure contemplates any suitable method for replacing a needle probe in a cryogenic device, including any suitable steps, which may include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

While the exemplary embodiments have been described in some detail for clarity of understanding and by way of example, a number of modifications, changes, and adaptations may be implemented and/or will be obvious to those as skilled in the art.

What is claimed is:

1. A cryogenic device comprising:
   a cartridge holder for holding a cryogen cartridge comprising a cryogen, wherein the cryogen cartridge is coupleable to a cryogen pathway; and
   a probe receptacle configured to receive a needle probe, wherein the probe receptacle is configured to couple the needle probe to the cryogen cartridge via the cryogen pathway, and wherein the needle probe comprises:
   one or more needles each having a needle lumen disposed therein;
   a first sealing element at a proximal side of a first location;
   a second sealing element at a distal side of the first location;
   a supply valve between the cryogen cartridge and the second sealing element, the supply valve configured to transition from an open position to a closed position; and
   a probe extension extending proximally, the probe extension having a probe lumen disposed therein, the probe lumen including an elongate element that extends from a proximal end to a distal end, wherein the probe lumen is coupled to:
   the needle lumens at the distal end, and
   an inlet of the cryogen pathway at the first location in between the proximal end and the distal end so as to reduce an outward force on the needle probe,
   wherein the first sealing element and the second sealing element seal the proximal end and the distal end of the probe receptacle from venting to ambient air when the supply valve is in the open position and when the supply valve is in the closed position, and wherein the first sealing element and the second sealing element do not translate with the supply valve in the open position and the closed position so as to stabilize pressure within the probe receptacle.

2. The cryogenic device of claim 1, wherein the first and second sealing elements are configured to seal the probe receptacle at the proximal and distal sides of the first location.

3. The cryogenic device of claim 2, wherein the first and second sealing elements are O-rings.

4. The cryogenic device of claim 1, wherein the supply valve is disposed along the cryogen pathway between the cryogen cartridge and the probe receptacle.

5. The cryogenic device of claim 1, wherein the cryogen pathway comprises a bore through an internal chassis, wherein an interior surface of the cryogen pathway comprises a metal material configured to reduce formation of bubbles from vaporization of the cryogen.

6. The cryogenic device of claim 1, wherein the cartridge holder and the probe receptacle are housed in a handpiece capable of being held by a user.

7. The cryogenic device of claim 6, further comprising a piercing point integrated into the handpiece, wherein the piercing point is configured to pierce the cryogen cartridge when the cryogen cartridge is disposed within the cartridge holder.

8. The cryogenic device of claim 6, wherein the handpiece comprises an elongate housing extending along an axis, the elongate housing of the handpiece comprising a movable cartridge door fixed to the elongate housing along the axis of the elongate housing, wherein the cartridge door is configured to move from an open position for allowing the cartridge holder to receive the cryogen cartridge to a closed position for securing the cryogen cartridge within the elongate housing.

9. The cryogenic device of claim 8, wherein the cartridge door is fixed to the elongate housing such that it is configured to swivel from the open position to the closed position.

10. The cryogenic device of claim 6, wherein the handpiece comprises an elongate housing extending along an axis, and wherein the handpiece is configured to rest substantially horizontally along the axis on a charging cradle to receive charging energy from the charging cradle.

11. The cryogenic device of claim 6, further comprising a processor located within the handpiece, wherein the processor is configured to receive a probe descriptor information from the needle probe, wherein the processor is further configured to determine that the needle probe is of a first probe type of a plurality of probe types.

12. The cryogenic device of claim 1, further comprising a passageway terminating at a proximal end of the probe extension, wherein the passageway is exposed to ambient air such that the proximal end of the probe extension is exposed to ambient air.

13. The cryogenic device of claim 1, wherein the one or more needles include one or more depressions or projections configured to make one or more portions of the needles echogenic so as to allow for visualization of the needles using ultrasound.

14. The cryogenic device of claim 13, wherein the depressions or projections have a polygonal design.

15. A cryogenic device comprising:
   a cartridge holder for holding a cryogen cartridge comprising a cryogen, wherein the cryogen cartridge is coupleable to a cryogen pathway;
   a probe receptacle configured to receive a probe extension of a needle probe, the probe extension having a proximal end and a distal end, wherein the probe receptacle is configured to receive the proximal end of the probe extension, and wherein the probe receptacle comprises:
   a first sealing element and a second sealing element for sealing the probe receptacle;
   a supply valve between the cryogen cartridge and the second sealing element, the supply valve configured to transition from an open position to a closed position; and
   a probe receptacle configured to, when the probe extension is secured to the probe receptacle, couple a lumen of the probe extension to an inlet of the cryogen pathway and introduce the cryogen into the lumen of the probe extension, wherein the probe receptacle couples to the inlet of the cryogen pathway at a first location between the proximal end and the distal end of the probe extension, wherein the first location is disposed between the first sealing element and the second sealing element,
   wherein the first sealing element and the second sealing element seal the proximal end and the distal end of the probe receptacle from venting to ambient air when the supply valve is in the open position and when the supply valve is in the closed position, and wherein the first sealing element and the second sealing element do not translate with the supply valve in the open position and the closed position so as to stabilize pressure within the probe receptacle.

* * * * *